United States Patent
Hoey et al.

(10) Patent No.: US 12,096,967 B2
(45) Date of Patent: *Sep. 24, 2024

(54) VAPOR ABLATION SYSTEMS AND METHODS

(71) Applicant: Boston Scientific Scimed, Inc., Maple Grove, MN (US)

(72) Inventors: Michael Hoey, Shoreview, MN (US); Roger Noel Hastings, Naples, FL (US); Mark Schrom, Forest Lake, MN (US); Steven Carlson, St. Paul, MN (US); Matthew Byrne, Minneapolis, MN (US); Karliam C. Woo, Maple Grove, MN (US); Eric Jerke, Dayton, MN (US); Richard Charles Kravik, Champlin, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 59 days.

This patent is subject to a terminal disclaimer.

(21) Appl. No.: 17/646,530

(22) Filed: Dec. 30, 2021

(65) Prior Publication Data

US 2022/0125498 A1    Apr. 28, 2022

Related U.S. Application Data

(63) Continuation of application No. 15/851,333, filed on Dec. 21, 2017, now Pat. No. 11,246,640.
(Continued)

(51) Int. Cl.
*A61B 18/04*    (2006.01)
*A61B 5/06*    (2006.01)
(Continued)

(52) U.S. Cl.
CPC .............. *A61B 18/04* (2013.01); *A61B 5/062* (2013.01); *A61B 2018/00273* (2013.01);
(Continued)

(58) Field of Classification Search
CPC .................... A61B 18/04; A61B 18/08; A61B 2018/00017; A61B 2018/00178;
(Continued)

(56) References Cited

U.S. PATENT DOCUMENTS

| 408,899 A | 8/1889 | Small |
| 1,719,750 A | 7/1929 | Bridge et al. |

(Continued)

FOREIGN PATENT DOCUMENTS

| CN | 2061443 U | 9/1990 |
| CN | 2418844 | 2/2001 |

(Continued)

OTHER PUBLICATIONS

Hai; Photoselective Vaporization Prostatectomy: A Palliative Treatment Option for Men with Urinary Obstruction Secondary to Prostate Cancer; PCRI Prost.Cancer Rsrch.Inst. Reprint.from PCRI Insights Nov. 2005, vol. 8(4); Dwnld from http://www.prostate-cancer.org/pcricms/node/233 on May 10, 2012; 4 pages.

(Continued)

*Primary Examiner* — Thomas A Giuliani
(74) *Attorney, Agent, or Firm* — Bookoff McAndrews, PLLC

(57) ABSTRACT

A vapor delivery device is provided that may include any of a number of features. One feature of the vapor delivery device is that it can apply condensable vapor energy to tissue, such as a prostate, to shrink, damage, denaturate tissues of the prostate. The vapor delivery device can include a handle portion and a cartridge portion. The cartridge portion can be configured to be inserted into a lumen of the (Continued)

handle portion to align and position a vapor coil of the cartridge portion within a RF coil of the handle portion. Methods associated with use of the energy delivery probe are also covered.

18 Claims, 14 Drawing Sheets

Related U.S. Application Data

(60) Provisional application No. 62/538,517, filed on Jul. 28, 2017, provisional application No. 62/437,617, filed on Dec. 21, 2016.

(51) Int. Cl.
    *A61B 18/00* (2006.01)
    *A61B 90/00* (2016.01)

(52) U.S. Cl.
    CPC .......... *A61B 2018/00434* (2013.01); *A61B 2018/00547* (2013.01); *A61B 2018/00577* (2013.01); *A61B 2018/00708* (2013.01); *A61B 2018/00791* (2013.01); *A61B 2018/00821* (2013.01); *A61B 2018/00982* (2013.01); *A61B 2018/048* (2013.01); *A61B 2090/062* (2016.02)

(58) Field of Classification Search
    CPC  A61B 2018/00005; A61B 2018/00791; A61B 2018/00821; A61B 2018/048; A61B 2018/00434; A61B 2018/00547; A61B 2018/00577; A61B 2018/00029; A61B 2018/00041; A61B 2018/00994; A61B 2018/1435; A61B 5/062; A61B 2090/062; A61B 2018/00797; A61B 2018/00815; A61B 2018/00809
    USPC .... 606/27–29, 41; 607/96, 98, 99, 103–105, 607/113, 115, 116
    See application file for complete search history.

(56) References Cited

U.S. PATENT DOCUMENTS

| | | |
|---|---|---|
| 4,672,963 A | 6/1987 | Barken |
| 4,920,982 A | 5/1990 | Goldstein |
| 4,950,267 A | 8/1990 | Ishihara et al. |
| 5,117,482 A | 5/1992 | Hauber |
| 5,222,185 A | 6/1993 | McCord, Jr. |
| 5,249,585 A | 10/1993 | Turner et al. |
| 5,300,099 A | 4/1994 | Rudie |
| 5,312,399 A | 5/1994 | Hakky et al. |
| 5,330,518 A | 7/1994 | Neilson et al. |
| 5,366,490 A | 11/1994 | Edwards et al. |
| 5,370,609 A | 12/1994 | Drasler et al. |
| 5,370,675 A | 12/1994 | Edwards et al. |
| 5,370,677 A | 12/1994 | Rudie et al. |
| 5,385,544 A | 1/1995 | Edwards et al. |
| 5,409,453 A | 4/1995 | Lundquist et al. |
| 5,413,588 A | 5/1995 | Rudie et al. |
| 5,421,819 A | 6/1995 | Edwards et al. |
| 5,435,805 A | 7/1995 | Edwards et al. |
| 5,464,437 A | 11/1995 | Reid et al. |
| 5,470,308 A | 11/1995 | Edwards et al. |
| 5,470,309 A | 11/1995 | Edwards et al. |
| 5,484,400 A | 1/1996 | Edwards et al. |
| 5,499,998 A | 3/1996 | Meade |
| 5,531,676 A | 7/1996 | Edwards et al. |
| 5,531,763 A | 7/1996 | Mastri et al. |
| 5,542,915 A | 8/1996 | Edwards et al. |
| 5,542,916 A | 8/1996 | Hirsch et al. |
| 5,545,171 A | 8/1996 | Sharkey et al. |
| 5,549,644 A | 8/1996 | Lundquist et al. |
| 5,554,110 A | 9/1996 | Edwards et al. |
| 5,556,377 A | 9/1996 | Rosen et al. |
| 5,558,673 A | 9/1996 | Edwards et al. |
| 5,588,960 A | 12/1996 | Edwards et al. |
| 5,591,125 A | 1/1997 | Edwards et al. |
| 5,599,294 A | 2/1997 | Edwards et al. |
| 5,601,591 A | 2/1997 | Edwards et al. |
| 5,628,770 A | 5/1997 | Thome et al. |
| 5,630,794 A | 5/1997 | Lax et al. |
| 5,645,528 A | 7/1997 | Thome |
| 5,667,488 A | 9/1997 | Lundquist et al. |
| 5,672,153 A | 9/1997 | Lax et al. |
| 5,709,680 A | 1/1998 | Yates et al. |
| 5,720,718 A | 2/1998 | Rosen et al. |
| 5,720,719 A | 2/1998 | Edwards et al. |
| 5,776,176 A | 7/1998 | Rudie |
| 5,792,070 A | 8/1998 | Kauphusman et al. |
| 5,797,903 A | 8/1998 | Swanson et al. |
| 5,800,486 A | 9/1998 | Thome et al. |
| 5,807,395 A | 9/1998 | Mulier et al. |
| 5,830,179 A | 11/1998 | Mikus et al. |
| 5,843,144 A | 12/1998 | Rudie et al. |
| 5,849,011 A | 12/1998 | Jones et al. |
| 5,861,021 A | 1/1999 | Thome et al. |
| 5,871,481 A | 2/1999 | Kannenberg et al. |
| 5,873,877 A | 2/1999 | Mcgaffigan et al. |
| 5,897,553 A | 4/1999 | Mulier et al. |
| 5,899,932 A | 5/1999 | Dann et al. |
| 5,938,692 A | 8/1999 | Rudie |
| 5,944,715 A | 8/1999 | Goble et al. |
| 5,951,515 A | 9/1999 | Osterlind |
| 5,957,922 A | 9/1999 | Imran |
| 5,964,752 A | 10/1999 | Stone |
| 5,964,756 A | 10/1999 | McGaffigan et al. |
| 5,976,123 A | 11/1999 | Baumgardner et al. |
| 5,987,360 A | 11/1999 | Mcgrath et al. |
| 5,990,465 A | 11/1999 | Nakaoka et al. |
| 6,007,571 A | 12/1999 | Neilson et al. |
| 6,009,351 A | 12/1999 | Flachman |
| 6,017,358 A | 1/2000 | Yoon et al. |
| 6,017,361 A | 1/2000 | Mikus et al. |
| 6,036,631 A | 3/2000 | Mcgrath et al. |
| 6,036,713 A | 3/2000 | Kieturakis |
| 6,053,909 A | 4/2000 | Shadduck |
| 6,063,081 A | 5/2000 | Mulier et al. |
| 6,067,475 A | 5/2000 | Graves et al. |
| 6,077,257 A | 6/2000 | Edwards et al. |
| 6,113,593 A | 9/2000 | Tu et al. |
| 6,122,551 A | 9/2000 | Rudie et al. |
| 6,123,083 A | 9/2000 | Mcgrath et al. |
| 6,147,336 A | 11/2000 | Ushijima et al. |
| 6,148,236 A | 11/2000 | Dann |
| 6,156,036 A | 12/2000 | Sussman et al. |
| 6,161,049 A | 12/2000 | Rudie et al. |
| 6,179,805 B1 | 1/2001 | Sussman et al. |
| 6,179,836 B1 | 1/2001 | Eggers et al. |
| 6,206,847 B1 | 3/2001 | Edwards et al. |
| 6,210,404 B1 | 4/2001 | Shadduck |
| 6,223,085 B1 | 4/2001 | Dann et al. |
| 6,231,591 B1 | 5/2001 | Desai |
| 6,238,389 B1 | 5/2001 | Paddock et al. |
| 6,238,391 B1 | 5/2001 | Olsen et al. |
| 6,238,393 B1 | 5/2001 | Mulier et al. |
| 6,241,702 B1 | 6/2001 | Lundquist et al. |
| 6,258,087 B1 | 7/2001 | Edwards et al. |
| 6,272,384 B1 | 8/2001 | Simon et al. |
| 6,287,297 B1 | 9/2001 | Woodruff et al. |
| 6,293,792 B1 * | 9/2001 | Hanson .............. A61C 17/0202 433/80 |
| 6,302,903 B1 | 10/2001 | Mulier et al. |
| 6,312,391 B1 | 11/2001 | Ramadhyani et al. |
| 6,315,777 B1 | 11/2001 | Comben |
| 6,348,039 B1 | 2/2002 | Flachman et al. |
| 6,398,759 B1 | 6/2002 | Sussman et al. |
| 6,409,722 B1 | 6/2002 | Hoey et al. |
| 6,423,027 B1 | 7/2002 | Gonon |
| 6,440,127 B2 | 8/2002 | Mcgovern et al. |
| 6,461,296 B1 | 10/2002 | Desai |
| 6,494,902 B2 | 12/2002 | Hoey et al. |

(56) References Cited

U.S. PATENT DOCUMENTS

| | | |
|---|---|---|
| 6,496,737 B2 | 12/2002 | Rudie et al. |
| 6,508,816 B2 | 1/2003 | Shadduck |
| 6,517,534 B1 | 2/2003 | Mcgovern et al. |
| 6,524,270 B1 | 2/2003 | Bolmsjoe et al. |
| 6,537,248 B2 | 3/2003 | Mulier et al. |
| 6,537,272 B2 | 3/2003 | Christopherson et al. |
| 6,544,211 B1 | 4/2003 | Andrew et al. |
| 6,551,300 B1 | 4/2003 | Mcgaffigan |
| 6,565,561 B1 | 5/2003 | Goble et al. |
| 6,575,929 B2 | 6/2003 | Sussman et al. |
| 6,575,968 B1 | 6/2003 | Eggers et al. |
| 6,579,270 B2 | 6/2003 | Sussman et al. |
| 6,589,201 B1 | 7/2003 | Sussman et al. |
| 6,607,529 B1 | 8/2003 | Jones et al. |
| 6,638,275 B1 | 10/2003 | Mcgaffigan et al. |
| 6,640,139 B1 | 10/2003 | Ueberle |
| 6,669,694 B2 | 12/2003 | Shadduck |
| 6,676,628 B2 | 1/2004 | Sussman et al. |
| 6,706,039 B2 | 3/2004 | Mulier et al. |
| 6,716,252 B2 | 4/2004 | Lazarovitz et al. |
| 6,719,738 B2 | 4/2004 | Mehier |
| 6,726,696 B1 | 4/2004 | Houser et al. |
| 6,730,079 B2 | 5/2004 | Lovewell |
| 6,736,810 B2 | 5/2004 | Hoey et al. |
| 6,740,108 B1 | 5/2004 | Just et al. |
| 6,760,616 B2 | 7/2004 | Hoey et al. |
| 6,780,178 B2 | 8/2004 | Palanker et al. |
| 6,827,718 B2 | 12/2004 | Hutchins et al. |
| 6,855,141 B2 | 2/2005 | Lovewell |
| 6,887,237 B2 | 5/2005 | Mcgaffigan |
| 6,905,475 B2 | 6/2005 | Hauschild et al. |
| 6,911,028 B2 | 6/2005 | Shadduck |
| 6,969,376 B2 | 11/2005 | Takagi et al. |
| 6,974,455 B2 | 12/2005 | Garabedian et al. |
| 7,014,652 B2 | 3/2006 | Cioanta et al. |
| 7,041,121 B1 | 5/2006 | Williams et al. |
| 7,066,935 B2 | 6/2006 | Swoyer et al. |
| 7,089,064 B2 | 8/2006 | Manker et al. |
| 7,130,697 B2 | 10/2006 | Chornenky et al. |
| 7,238,182 B2 | 7/2007 | Swoyer et al. |
| 7,247,155 B2 | 7/2007 | Hoey et al. |
| 7,261,709 B2 | 8/2007 | Swoyer et al. |
| 7,261,710 B2 | 8/2007 | Elmouelhi et al. |
| 7,322,974 B2 | 1/2008 | Swoyer et al. |
| 7,328,068 B2 | 2/2008 | Spinelli et al. |
| 7,328,069 B2 | 2/2008 | Gerber |
| 7,335,197 B2 | 2/2008 | Sage et al. |
| 7,340,300 B2 | 3/2008 | Christopherson et al. |
| 7,369,894 B2 | 5/2008 | Gerber |
| 7,429,262 B2 | 9/2008 | Woloszko et al. |
| 7,437,194 B2 | 10/2008 | Skwarek et al. |
| 7,470,228 B2 | 12/2008 | Connors et al. |
| 7,549,987 B2 | 6/2009 | Shadduck |
| 7,865,250 B2 | 1/2011 | Mrva et al. |
| 7,894,913 B2 | 2/2011 | Boggs et al. |
| 7,959,577 B2 | 6/2011 | Schmitz et al. |
| 8,048,069 B2 | 11/2011 | Skwarek et al. |
| 8,216,217 B2 | 7/2012 | Sharkey et al. |
| 8,244,327 B2 | 8/2012 | Fichtinger et al. |
| 8,251,985 B2 | 8/2012 | Hoey et al. |
| 8,272,383 B2 | 9/2012 | Hoey et al. |
| 8,273,079 B2 | 9/2012 | Hoey et al. |
| 8,301,264 B2 | 10/2012 | Achenbach et al. |
| 8,313,485 B2 | 11/2012 | Shadduck |
| 8,372,065 B2 | 2/2013 | Hoey et al. |
| 8,388,611 B2 | 3/2013 | Shadduck et al. |
| 8,409,109 B2 | 4/2013 | Tiesma et al. |
| 8,419,723 B2 | 4/2013 | Shadduck et al. |
| 8,550,743 B2 | 10/2013 | Bonde et al. |
| 8,585,692 B2 | 11/2013 | Shadduck et al. |
| 8,632,530 B2 | 1/2014 | Hoey et al. |
| 8,740,957 B2 | 6/2014 | Masotti |
| 8,801,702 B2 | 8/2014 | Hoey et al. |
| 8,814,856 B2 * | 8/2014 | Elmouelhi ......... A61B 18/1492 606/41 |
| 8,900,223 B2 | 12/2014 | Shadduck |
| 9,198,708 B2 | 12/2015 | Hoey et al. |
| 9,345,507 B2 | 5/2016 | Hoey et al. |
| 9,526,555 B2 | 12/2016 | Hoey et al. |
| 9,833,277 B2 | 12/2017 | Hoey et al. |
| 9,895,185 B2 | 2/2018 | Hoey et al. |
| 10,335,222 B2 | 7/2019 | Hoey et al. |
| 11,246,640 B2 * | 2/2022 | Hoey ................... A61B 18/04 |
| 2002/0078956 A1 | 6/2002 | Sharpe et al. |
| 2002/0111617 A1 | 8/2002 | Cosman et al. |
| 2002/0177846 A1 | 11/2002 | Mulier et al. |
| 2003/0028172 A1 | 2/2003 | Epstein et al. |
| 2003/0069575 A1 | 4/2003 | Chin et al. |
| 2003/0092689 A1 | 5/2003 | Escandon et al. |
| 2003/0097126 A1 | 5/2003 | Woloszko et al. |
| 2003/0130575 A1 | 7/2003 | Desai |
| 2003/0206730 A1 | 11/2003 | Golan |
| 2004/0006334 A1 | 1/2004 | Beyar et al. |
| 2004/0068306 A1 | 4/2004 | Shadduck |
| 2004/0186422 A1 | 9/2004 | Rioux et al. |
| 2004/0220462 A1 | 11/2004 | Schwartz |
| 2004/0230316 A1 | 11/2004 | Cioanta et al. |
| 2004/0267340 A1 | 12/2004 | Cioanta et al. |
| 2005/0096629 A1 | 5/2005 | Gerber et al. |
| 2005/0124915 A1 | 6/2005 | Eggers et al. |
| 2005/0149020 A1 | 7/2005 | Jahng |
| 2005/0159676 A1 | 7/2005 | Taylor et al. |
| 2006/0089636 A1 | 4/2006 | Christopherson et al. |
| 2006/0135955 A1 | 6/2006 | Shadduck |
| 2006/0178670 A1 | 8/2006 | Woloszko et al. |
| 2006/0224154 A1 | 10/2006 | Shadduck et al. |
| 2006/0224169 A1 | 10/2006 | Weisenburgh, II et al. |
| 2006/0253069 A1 | 11/2006 | Li et al. |
| 2006/0276871 A1 | 12/2006 | Lamson et al. |
| 2007/0032785 A1 | 2/2007 | Diederich et al. |
| 2007/0038089 A1 | 2/2007 | Hatano et al. |
| 2007/0142846 A1 | 6/2007 | Catanese et al. |
| 2007/0179491 A1 | 8/2007 | Kratoska et al. |
| 2007/0197864 A1 | 8/2007 | Dejima et al. |
| 2007/0213703 A1 | 9/2007 | Naam et al. |
| 2008/0021484 A1 | 1/2008 | Catanese et al. |
| 2008/0021485 A1 | 1/2008 | Catanese et al. |
| 2008/0033232 A1 | 2/2008 | Catanese et al. |
| 2008/0033458 A1 | 2/2008 | Mclean et al. |
| 2008/0033488 A1 | 2/2008 | Catanese et al. |
| 2008/0039833 A1 | 2/2008 | Catanese et al. |
| 2008/0039872 A1 | 2/2008 | Catanese et al. |
| 2008/0039874 A1 | 2/2008 | Catanese et al. |
| 2008/0039875 A1 | 2/2008 | Catanese et al. |
| 2008/0039876 A1 | 2/2008 | Catanese et al. |
| 2008/0039893 A1 | 2/2008 | Mclean et al. |
| 2008/0039894 A1 | 2/2008 | Catanese et al. |
| 2008/0046045 A1 | 2/2008 | Yon et al. |
| 2008/0110457 A1 | 5/2008 | Barry et al. |
| 2008/0132826 A1 | 6/2008 | Shadduck et al. |
| 2008/0188811 A1 | 8/2008 | Kim |
| 2008/0208187 A1 | 8/2008 | Bhushan et al. |
| 2008/0208246 A1 * | 8/2008 | Livneh ............... A61B 18/1445 606/205 |
| 2008/0214956 A1 | 9/2008 | Briggs et al. |
| 2008/0217325 A1 | 9/2008 | Von et al. |
| 2008/0249399 A1 | 10/2008 | Appling et al. |
| 2008/0262491 A1 | 10/2008 | Swoyer et al. |
| 2008/0269737 A1 | 10/2008 | Elmouelhi et al. |
| 2008/0269862 A1 | 10/2008 | Elmouelhi et al. |
| 2008/0275440 A1 | 11/2008 | Kratoska et al. |
| 2008/0297287 A1 | 12/2008 | Shachar et al. |
| 2008/0312497 A1 | 12/2008 | Elmouelhi et al. |
| 2009/0018553 A1 | 1/2009 | Mclean et al. |
| 2009/0054871 A1 | 2/2009 | Sharkey et al. |
| 2009/0138001 A1 | 5/2009 | Barry et al. |
| 2009/0149846 A1 | 6/2009 | Hoey et al. |
| 2009/0199855 A1 | 8/2009 | Davenport |
| 2009/0216220 A1 | 8/2009 | Hoey et al. |
| 2009/0227998 A1 | 9/2009 | Aljuri et al. |
| 2009/0306640 A1 | 12/2009 | Glaze et al. |
| 2010/0016757 A1 | 1/2010 | Greenburg et al. |
| 2010/0049031 A1 | 2/2010 | Fruland et al. |
| 2010/0094270 A1 | 4/2010 | Sharma |

(56) References Cited

U.S. PATENT DOCUMENTS

| | | |
|---|---|---|
| 2010/0114083 A1 | 5/2010 | Sharma et al. |
| 2010/0179416 A1 | 7/2010 | Hoey et al. |
| 2010/0193568 A1 | 8/2010 | Scheib et al. |
| 2010/0204688 A1 | 8/2010 | Joey et al. |
| 2010/0256636 A1 | 10/2010 | Fernandez et al. |
| 2010/0262133 A1 | 10/2010 | Hoey et al. |
| 2010/0262137 A1 | 10/2010 | Nye et al. |
| 2010/0292767 A1 | 11/2010 | Hoey et al. |
| 2010/0298948 A1 | 11/2010 | Hoey et al. |
| 2010/0312237 A1 | 12/2010 | Habib et al. |
| 2011/0060328 A1 | 3/2011 | Skwarek et al. |
| 2011/0077628 A1 | 3/2011 | Hoey et al. |
| 2011/0106072 A1 | 5/2011 | Sundquist et al. |
| 2011/0160648 A1 | 6/2011 | Hoey |
| 2011/0264176 A1 | 10/2011 | Jackson et al. |
| 2011/0319759 A1 | 12/2011 | Liu et al. |
| 2012/0116392 A1* | 5/2012 | Willard .............. A61B 18/1492 606/41 |
| 2012/0259271 A1 | 10/2012 | Shadduck et al. |
| 2012/0265276 A1 | 10/2012 | Curley |
| 2013/0006231 A1 | 1/2013 | Sharma et al. |
| 2013/0066308 A1 | 3/2013 | Landman |
| 2013/0072855 A1 | 3/2013 | Sherry et al. |
| 2013/0074847 A1 | 3/2013 | Hoey et al. |
| 2013/0172867 A1 | 7/2013 | Shadduck et al. |
| 2013/0261692 A1 | 10/2013 | Cardinal et al. |
| 2014/0039356 A1 | 2/2014 | Sachs et al. |
| 2014/0200568 A1 | 7/2014 | Sharma et al. |
| 2014/0276713 A1* | 9/2014 | Hoey .................... A61B 18/04 607/96 |
| 2014/0288543 A1* | 9/2014 | Hoey .................... A61B 18/04 606/27 |
| 2014/0354381 A1 | 12/2014 | Kohlhafer |
| 2015/0025515 A1 | 1/2015 | Hoey et al. |
| 2015/0126990 A1 | 5/2015 | Sharma et al. |
| 2015/0157384 A1 | 6/2015 | Hoey et al. |
| 2016/0015445 A1 | 1/2016 | Hoey et al. |
| 2016/0081736 A1 | 3/2016 | Hoey et al. |
| 2016/0220296 A1 | 8/2016 | Hastings et al. |
| 2016/0270838 A1 | 9/2016 | Hastings et al. |
| 2016/0331435 A1 | 11/2016 | Hoey et al. |
| 2016/0354140 A1 | 12/2016 | Sharma et al. |
| 2017/0056089 A1 | 3/2017 | Hoey et al. |
| 2017/0231678 A1 | 8/2017 | Sharma |
| 2018/0360523 A1 | 12/2018 | Hastings et al. |

FOREIGN PATENT DOCUMENTS

| | | |
|---|---|---|
| CN | 101072544 A | 11/2007 |
| CN | 101257855 A | 9/2008 |
| CN | 101006939 C | 11/2008 |
| CN | 101491458 A | 7/2009 |
| CN | 101803947 A | 8/2010 |
| JP | H07507696 A | 8/1995 |
| JP | H08501957 A | 3/1996 |
| JP | H08504613 A | 5/1996 |
| JP | H11318925 A | 11/1999 |
| JP | 2000005191 A | 1/2000 |
| JP | 2000014663 A | 1/2000 |
| JP | 2001500763 A | 1/2001 |
| JP | 2002035004 A | 2/2002 |
| JP | 2005137916 A | 6/2005 |
| JP | 7129980 B2 | 9/2022 |
| WO | 9210142 A1 | 6/1992 |
| WO | 0124715 A1 | 4/2001 |
| WO | 03088851 A1 | 10/2003 |
| WO | 03096871 A2 | 11/2003 |
| WO | 2006004482 A1 | 1/2006 |
| WO | 2008083407 A1 | 7/2008 |
| WO | 2010080467 A2 | 7/2010 |
| WO | 2013160772 A2 | 10/2013 |
| WO | 2017106843 A1 | 6/2017 |

OTHER PUBLICATIONS

Hoey et al.; U.S. Appl. No. 15/864,957 entitled "Transperineal Vapor ablation systems and methods," filed Jan. 8, 2018.

Hoey et al.; U.S. Appl. No. 15/900,295 entitled "Systems and methods for prostate treatment," filed Feb. 20, 2018.

Nguyen et al; Updated results of magnetic resonance imaging guided partial prostate brachytherapy for favorable risk prostate cancer: implications for focal therapy; J. Urol.; 188(4); pp. 1151-1156; Oct. 2012.

US 5,326,343 A, Jul. 1994, Rudie et al. (withdrawn).

* cited by examiner

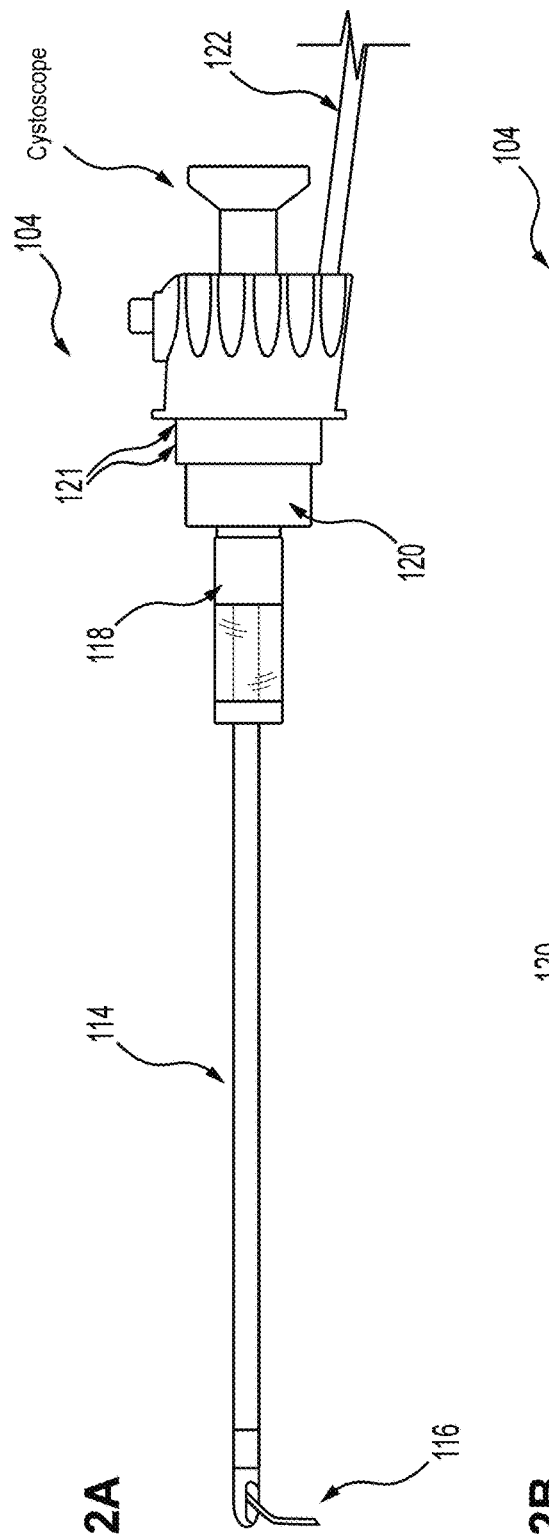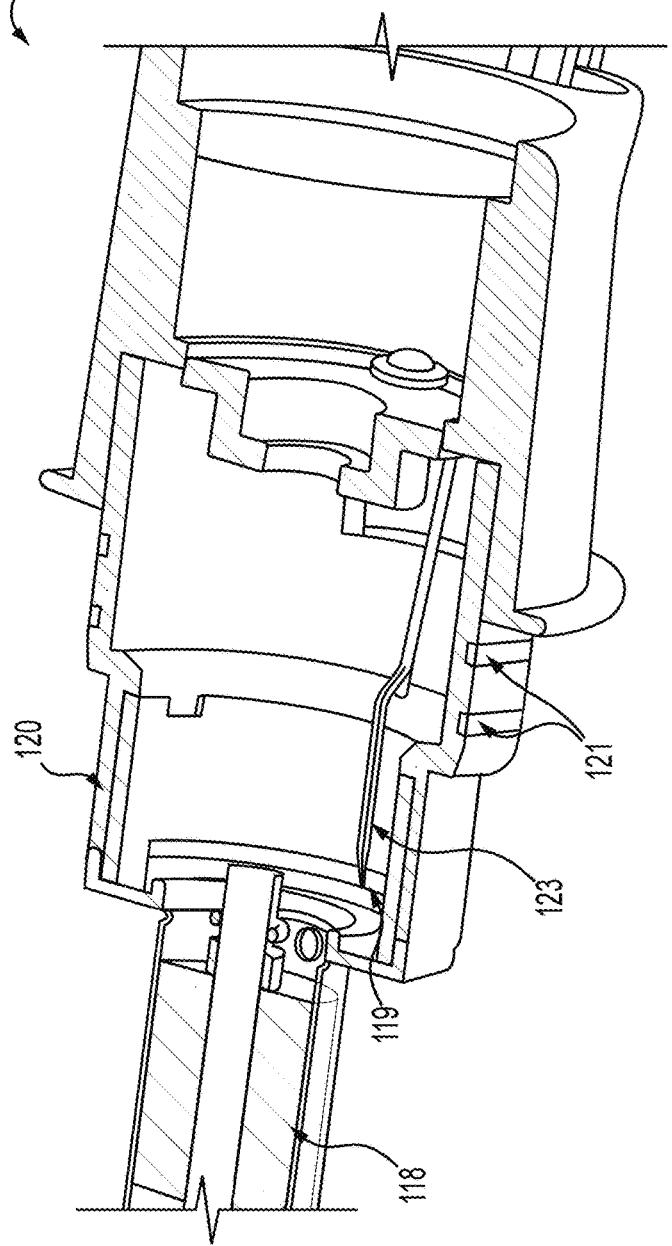
FIG. 2A
FIG. 2B

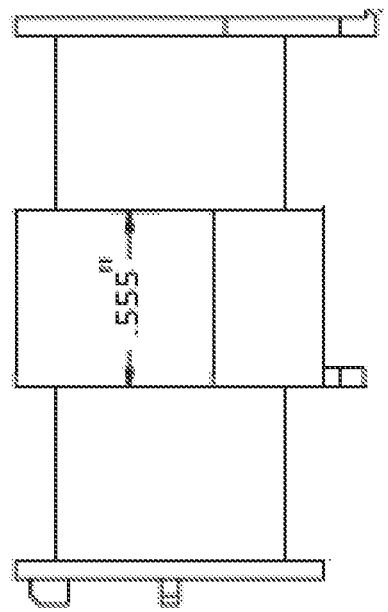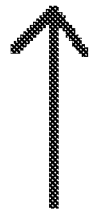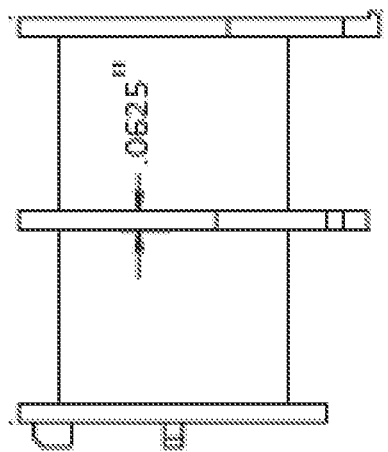
FIG. 7

VAPOR ABLATION SYSTEMS AND METHODS

CROSS REFERENCE TO RELATED APPLICATIONS

This application is a continuation of and claims the benefit of priority to U.S. patent application Ser. No. 15/851,333, filed Dec. 21, 2017, issued as U.S. Pat. No. 11,246,640, which claims priority to U.S. Provisional Application No. 62/437,617, filed Dec. 21, 2016, and to U.S. Provisional Application No. 62/538,517, filed Jul. 28, 2017, all of which are herein incorporated by reference in their entireties.

This application is related to U.S. patent application Ser. No. 14/773,853, filed Sep. 9, 2015, and International Patent Application No. PCT/US2016/067558, filed Dec. 19, 2016, both of which are herein incorporated by reference in their entirety.

INCORPORATION BY REFERENCE

All publications, including patents and patent applications, mentioned in this specification are herein incorporated by reference in their entirety to the same extent as if each individual publication was specifically and individually indicated to be incorporated by reference.

FIELD

The present invention relates to devices and related methods for treatment of the prostate using a minimally invasive approach.

BACKGROUND

The prostate early in life is the size and shape of a walnut and prior to the enlargement resulting from BPH, weighs about 20 grams. Prostate enlargement appears to be a normal process. With age, the prostate gradually increases in size to twice or more its normal size. The fibromuscular tissue of the outer prostatic capsule restricts expansion after the gland reaches a certain size. Because of such restriction on expansion, the intracapsular tissue will compress against and constrict the prostatic urethra, thus causing resistance to urine flow.

The prostate can be classified into three zones: the peripheral zone, transition zone, and central zone. Peripheral zone (PZ) comprises about 70% of the volume of a male's prostate. This sub-capsular portion of the posterior aspect of the prostate gland surrounds the distal urethra and 70% to 80% of cancers originate in the peripheral zone tissue. The central zone (CZ) surrounds the ejaculatory ducts and contains about 20-25% of the prostate volume. The central zone is often the site of inflammatory processes. The transition zone (TZ) is the site in which benign prostatic hyperplasia develops, and contains about 5-10% of the volume of glandular elements in a normal prostate, but can constitute up to 80% of such volume in cases of BPH. The transition zone includes two lateral prostate lobes and the periurethral gland region. There are natural barriers around the transition zone. i.e., the prostatic urethra, the anterior fibromuscular stroma FS, and a fibrous plane FP between the transition zone and peripheral zone. The anterior fibromuscular stroma FS or fibromuscular zone is predominantly fibromuscular tissue.

Approximately 70% to 80% of prostate cancers originate in the peripheral zone of the prostate and may be confined to the peripheral zone. In recent years, there has been an increased interest in focal therapy for prostate cancer, treating only regions of tissue in which cancer has been found following biopsies. Prior art focal therapy treatments, such as with RF ablation energy, may not confine the treatment to the peripheral zone tissue.

In patients with advanced prostate cancer a prostatectomy may be indicated, and an alternative to surgery is desired. A device is desired that can ablate the entire prostate or an entire lobe of the prostate via a transurethral approach. In this minimally invasive approach both transition and peripheral zones may be treated.

SUMMARY OF THE DISCLOSURE

Systems and methods for ablating peripheral zone tissues without ablating non-peripheral zone tissues are disclosed. A transurethral approach uses a vapor delivery device to access peripheral zone tissues that lie adjacent to the prostatic urethra.

Treatment of an entire peripheral zone may employ a vapor delivery needle that extends up to 2.5 cm from the delivery device shaft located in the urethra. Vapor may be delivered at multiple sites along the path of the needle using ultrasound and needle position sensor guidance.

The vapor delivery needle can be capable of controlled movement along its path, including stopping to deliver vapor. Systems and methods for controlling the movement of the needle in digital steps to any location within its reach are disclosed.

A blunted needle is disclosed that can penetrate the urethra wall during an initial shallow deployment, but will not penetrate the prostate capsule when the needle is advanced using pulses of current to the needle delivery solenoid.

Most prostate cancer arises in the peripheral zones. Vapor delivered through a needle to the peripheral zone will not cross tissue barriers to other zones of the prostate, where cancer may not be present.

It is possible to treat all zones of the prostate with a single transurethral vapor delivery device. A partial or total prostatectomy may be achieved during a single therapy treatment in which vapor is applied to some or all zones of the prostate.

A semi-disposable vapor delivery device is also disclosed in which the handle and cable are reusable, and the barrel with needle delivery shaft and attached water and flush lines comprise a disposable cartridge.

Inductive coupling is used to transmit RF power from an RF coil in the reusable handle to the vapor delivery coil in the disposable cartridge.

Magnetic coupling is employed to apply non-contact needle deployment forces from a solenoid coil in the handle to the needle deployment magnet in the disposable cartridge.

Inductive coupling can used to communicate temperature and identification data from the disposable to the reusable handle. Because the induction and force coils are cylindrically symmetric, their function is independent of orientation of the disposable, and so the cartridge may be rotated relative to the reusable handle, enabling application of therapy to the sides of the prostate without rotating the delivery device handle between the patient's legs. Sliding contacts between the disposable cartridge and reusable handle are also disclosed for vapor coil temperature readout.

Physicians may employ a single reusable handle to treat BPH or cancers by selecting a disposable cartridge that is designed for the indicated treatment. For example, a BPH cartridge may simpler and less costly than a prostate cancer cartridge because variable and controllable needle depth is not required for BPH treatment.

A vapor delivery device is provided, comprising a handle portion having a lumen and an RF coil disposed in the lumen, the RF coil being connectable to a source of RF energy, and a cartridge portion adapted to be inserted into the lumen of the handle portion, the cartridge portion including an elongate shaft adapted for insertion into a patient's urethra, a vapor delivery needle disposed in the elongate shaft, a vapor coil fluidly connected to the vapor delivery needle and to a fluid source, wherein insertion of the cartridge portion into the handle portion aligns and positions the vapor coil within the RF coil.

Application of RF energy to the RF coil can inductively generate vapor in the vapor coil when fluid is delivered from the fluid source to the vapor coil.

In some examples, the vapor delivery needle is adapted to deliver the vapor to tissue of the patient.

It is disclosed that the cartridge portion can further comprise a first solenoid coil and a second solenoid coil, a needle driver magnet attached to a proximal portion of the vapor delivery needle, the needle driver magnet being slidably disposed within the first solenoid coil when the vapor delivery needle is in a retracted position and slidably disposed within the second solenoid coil when the vapor delivery needle is in an extended position.

The device can further include a needle deployment switch on the handle portion.

In some examples, the vapor delivery needle can be fully deployed from the retracted position to the extended position with a press of the needle deployment switch. The vapor delivery needle can be incrementally deployed with each press of the needle deployment switch. For example, the vapor delivery needle can be deployed in 1 mm increments.

The device can further include a position sensor disposed on the vapor delivery needle, the position sensor being configured to determine a deployment position of the vapor delivery needle. A safety feature is provided in which the vapor delivery needle is prevented from advancing if the sensor indicates that the vapor delivery needle has not moved a desired incremental distance.

The vapor coil can comprise, for example, Inconel tubing.

The device can further include a latch configured to prevent lateral movement of the cartridge portion when it is inserted into the lumen of the handle portion.

The cartridge portion can be rotated when it is inserted into the lumen of the handle portion. This can be done to deliver vapor to multiple positions within the prostate, and to deliver vapor to both lobes of the prostate.

In one specific example, the delivery needle cannot extend more than 24 mm from the elongate shaft when in the extended position.

It is provided that the vapor delivery needle comprises an expandable balloon configured to prevent vapor from leaking from a puncture hole in the patient's tissue. The expandable balloon can be positioned in an indent of the vapor delivery needle. The expandable balloon is inflated with vapor during vapor delivery.

The vapor delivery device can further include an electronic controller configured to control delivery of RF energy to the RF coil.

It is also considered that the vapor delivery device can include a temperature sensor disposed an at outlet of the vapor coil and electrically coupled to the electronic controller, the temperature sensor being configured to measure a temperature of fluid or vapor in the outlet of the vapor coil.

As a safety measure, the electronic controller can be configured to trigger a shutdown of RF energy delivery if the measured temperature of fluid or vapor in the outlet is outside a preferred temperature range.

A method of delivering vapor to a prostate of a patient is also provided, comprising inserting a cartridge portion of a vapor delivery device into a lumen of a handle portion of the vapor delivery device to align and position a vapor coil of the cartridge portion within a RF coil of the handle portion, inserting an elongate shaft of the cartridge portion into a urethra of the patient, advancing a distal end of the elongate shaft to the prostatic urethra of the patient, extending a vapor delivery needle from the elongate shaft into the prostate of the patient, delivering a flow of fluid into the vapor coil, applying RF energy to the RF coil to inductively generate vapor within the vapor coil, and delivering the vapor to the prostate through the vapor delivery needle.

The extending step can comprise generating a magnetic field with at least one solenoid coil to extend the vapor delivery needle into the prostate.

The method can further comprise rotating the cartridge portion within the handle portion.

BRIEF DESCRIPTION OF THE DRAWINGS

In order to better understand the invention and to see how it may be carried out in practice, some preferred embodiments are next described, by way of non-limiting examples only, with reference to the accompanying drawings, in which like reference characters denote corresponding features consistently throughout similar embodiments in the attached drawings.

FIGS. 2A-2B show a disposable cartridge of the vapor delivery device.

FIG. 7 shows changes to the solenoids moving from a BPH device to a cancer device.

DETAILED DESCRIPTION OF THE INVENTION

In general, method for treating BPH or prostate cancer comprise transurethrally introducing a heated vapor interstitially into the interior of a prostate, wherein the vapor controllably ablates prostate tissue. The method can cause localized ablation of prostate tissue, and more particularly the applied thermal energy from vapor can be localized to ablate tissue adjacent the urethra without damaging prostate tissue that is not adjacent the urethra.

Transurethral vapor delivery devices of the present disclosure are used to transurethrally deliver vapor into the prostate of a patient. An elongate shaft of the device can be advanced into the urethra of the patient, and once positioned near the prostate within the prostatic urethra, a vapor delivery needle can be inserted into the prostate through the urethral wall. Vapor can then be delivered into the prostate through the vapor delivery needle.

Semi-Disposable Vapor Delivery Device

Figure 1A:
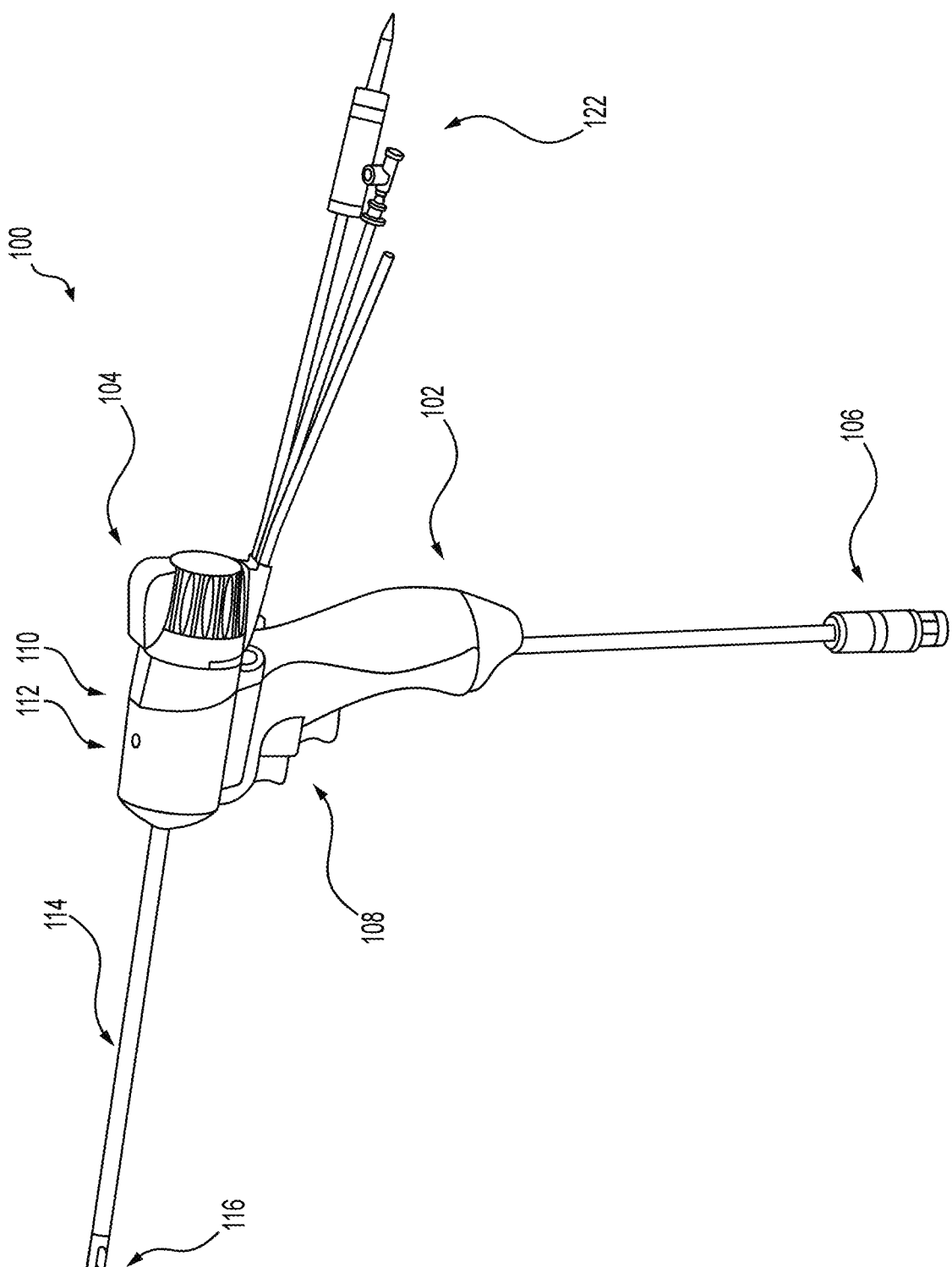
FIGS. 1A-IC show one embodiment of a transurethral vapor delivery device.
Figure 1B:
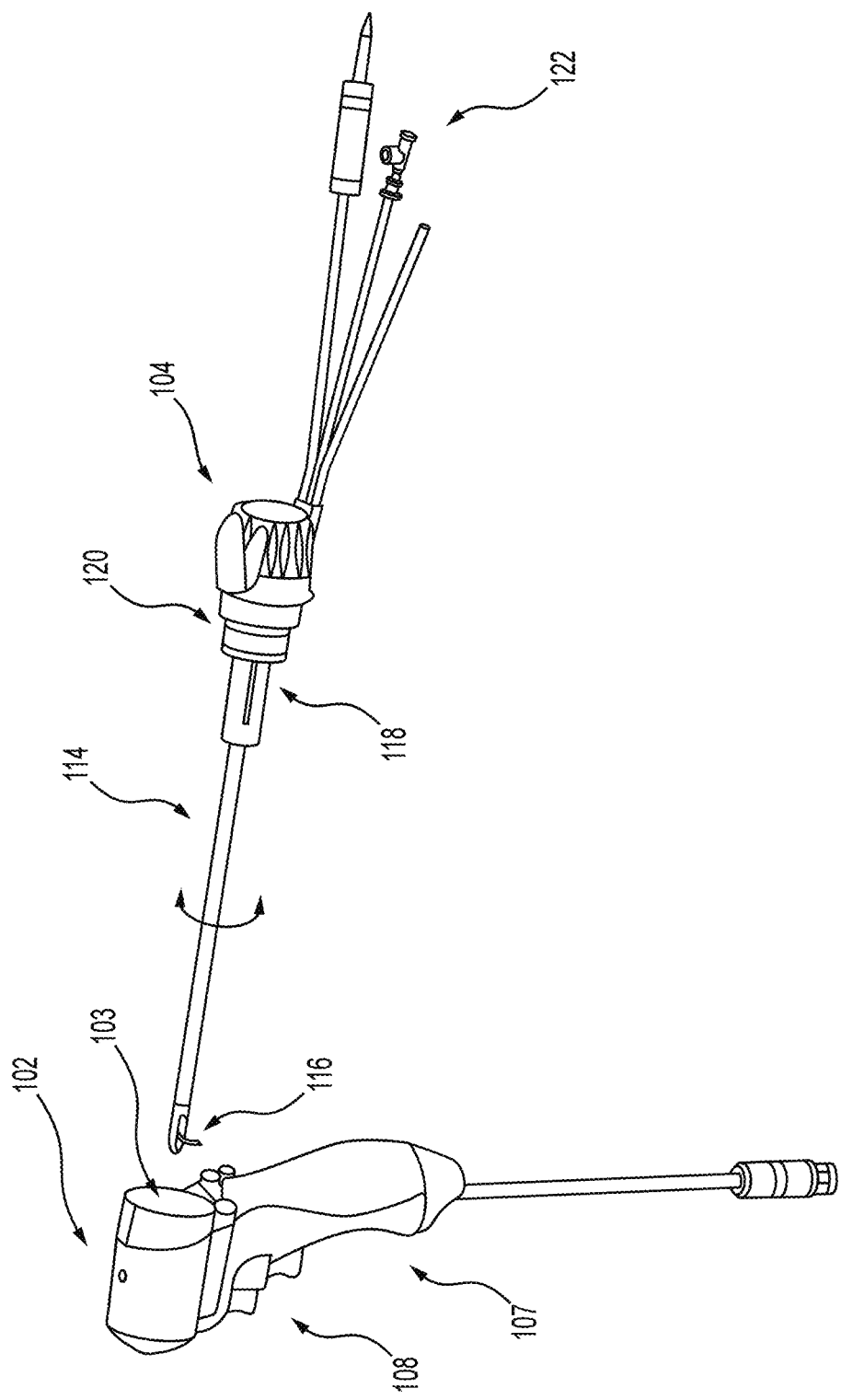

A transurethral vapor delivery device 100 is illustrated in FIG. 1A in its assembled form, while FIG. 1B shows a disassembled view to illustrate the reusable handle portion 102 and a disposable cartridge portion 104 of the vapor delivery device. The handle portion 102 of the vapor delivery device comprises a lumen 103, an electrical cable 106 that plugs into an RF generator (not shown), a grip portion 107, triggers 108 for actuation of flush, needle advance/retract, and RF power ON/OFF, an RF coil 110 (not shown) disposed in the lumen and configured to inductively produce vapor, and solenoid coils 112 (not shown) disposed in the handle portion and configured to advance and retract the vapor needle.

The RF generator can be configured to provide power and fluid to the transurethral vapor delivery device for the production of vapor. For example, the RF generator is configured to provide RF energy to the RF coil of the handle portion. The RF generator also can connect to the vapor delivery device described above to provide power and other components to the system vital for operation, such as irrigation/cooling fluid, suction, etc. The RF generator can include an electronic controller and a graphical user interface (GUI) to provide operating parameters and controls to the user during vapor therapy.

The RF generator can include an electrical connector which can provide RF current to the vapor delivery device, electrical signals to and from the switches of the vapor delivery device, measurements of, for example, the temperature of the vapor delivery device, and electrical signals to/from a controller of vapor delivery device, for example in its electrical connector, to identify the vapor delivery device, track its history of vapor delivery, and prevent excessive use of a given vapor delivery system. The RF generator may also contain a peristaltic pump that provides a flow of cooling/irrigation fluid such as saline to the vapor delivery device.

Figure 10:
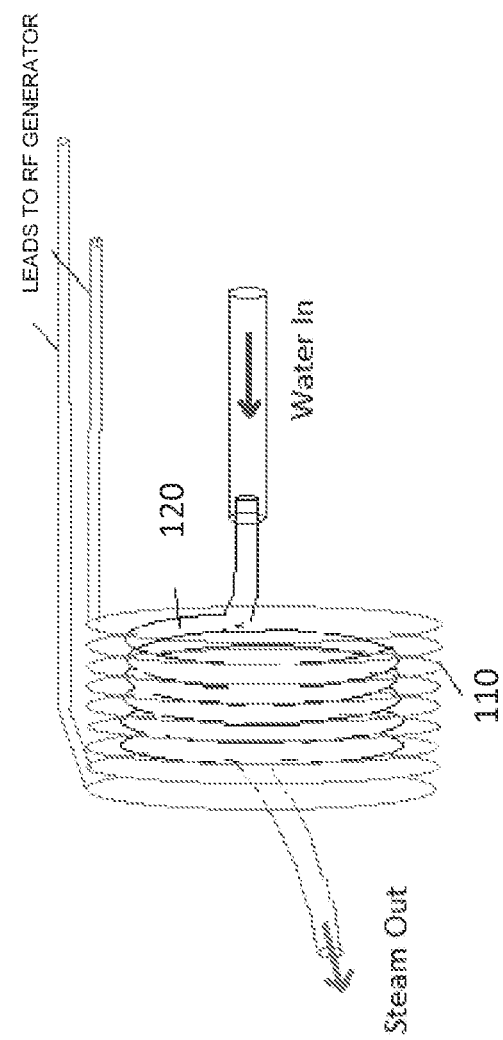
FIG. 10 illustrates an inductive vapor generator.

The disposable cartridge 104 comprises an elongate shaft 114 with lumens for a cystoscope and the vapor delivery needle 116, a needle driver magnet 118 (not shown) attached to the vapor delivery needle that is advanced or retracted by magnetic fields generated in the solenoid coils 112, vapor coil 120 in which water is inductively converted to vapor, and plastic tubing lines 122 for sterile water, saline flush, and bladder drain. The cartridge portion is adapted to be inserted into the lumen of the handle portion. When the cartridge portion is inserted into the handle portion, the vapor coil 120 of the cartridge is aligned and positioned within the RF coil 110 of the handle portion, or described alternatively, the RF coil 110 is aligned and positioned around the vapor coil 120 (as shown in FIG. 10). The elongate shaft 114 is sized and configured for insertion into a patient's urethra with a length that can extend to the patient's prostatic urethra and prostate. As illustrated in FIG. 1B, the cartridge may be rotated within the handle, facilitating delivery of vapor to the right and left lobes of the prostate without rotating the handle between the patient's legs.

In some procedures, the vapor therapy is at least partially guided by transrectal ultrasound (TRUS) imaging. In these procedures, the TRUS probe may prevent the vapor delivery device handle from being in the vertical, down position shown in FIG. 1A. In some alternative embodiments, the delivery device handle may extend upward from the barrel of the delivery device. In other embodiments, the barrel may be modified to contain the delivery device triggers and cable, and the handle portion eliminated altogether.

Figure 1C:
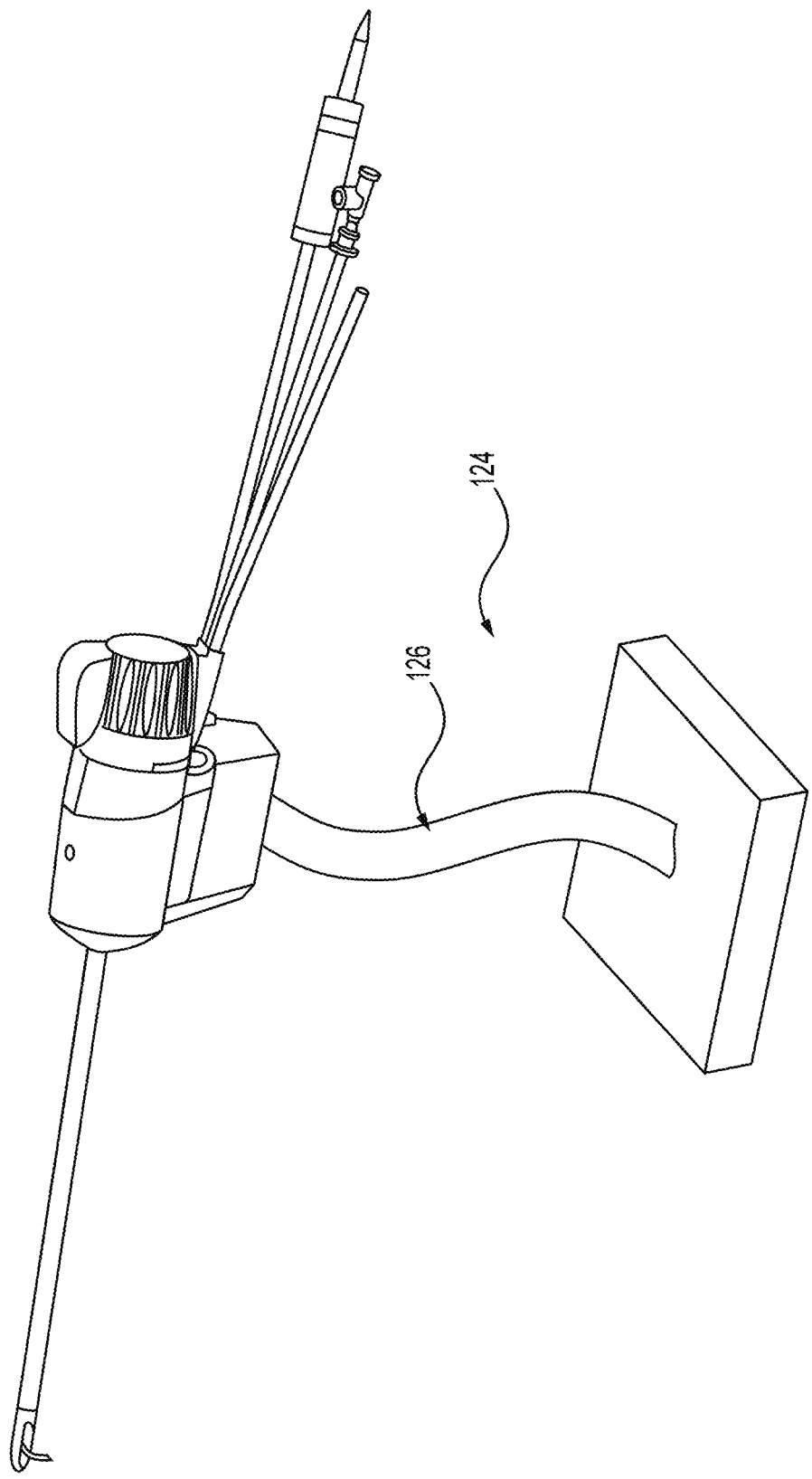

In some procedures, the delivery device needle may be advanced to deliver vapor at two or more sites after an initial puncture of the urethral wall. It is important for the vapor delivery needle to remain stable relative to the patient anatomy to prevent vapor leakage from an enlarged needle entrance hole. FIG. 1C shows an adjustable delivery device holder 124 that may be used to stabilize and hold the delivery device during needle delivery, advancement, and vapor delivery. This adjustable delivery device holder allows the operator to focus attention on image guided needle placement and therapy delivery. FIG. 1C shows an adjustable delivery device holder having a flexible, shapeable shaft 126 adjusted by the operator to maintain a position of the delivery device needle during therapy. In other embodiments, the holding device may be adjusted electronically. It may be configured to advance or retract the delivery device from the urethra. The handle in FIG. 1C may be as simple as an adjustable holding device shown in FIG. 1C, and as complex as a multi-axis robotic arm.

The disposable cartridge 104 is shown in cross-sectional views in FIGS. 2A-2B. The vapor delivery needle is rigidly attached to needle driver magnet 118 which is moved laterally by magnetic fields generated by coils in handle portion 102 (shown in FIG. 3). Vapor coil 120 is also shown in FIG. 2B. The disposable cartridge can include a resistance thermometer (RTD) 119 wired in series via a lead 123 with conductive metal rings 121. The RTD 119 can measure the temperature of the vapor exiting the vapor coil 120. In one embodiment, the RTD can be wrapped around the outlet of the vapor coil.

An inductive read-out coil can also be implemented in the reusable handle. A thermocouple can be placed on the RF coil in the reusable handle portion. Experience has shown that the first component to show signs of overheating (usually smoke) is the RF coil, even though it may be at a somewhat lower temperature than the adjacent inner coil. The RF coil is therefore a preferred location for a thermometer, preferably a thermocouple.

When the disposable cartridge 104 is inserted into the reusable handle portion 102, the cartridge can engage with canted coils in the handle. The cartridge insertion and retraction force may be specified in a tight range so that all cartridges fall into a repeatable mechanical force range. The canted coils serve as a sliding electrical contact, enabling rotation of the cartridge within the handle while maintaining electrical contact of the RTD outlet thermometer leads from the cartridge to the handle. There is some variability in the contact resistance between the rings and coils as the cartridge is rotated. However, an accurate temperature measurement is not required during rotation, so the contact resistance, or any change in contact resistance during rotation, may be zeroed out in software. The outlet thermometer is shown as an RTD, but other miniature sensors such as thermistors or thermocouples may be employed.

The vapor coil shown in FIG. 2B is connected to a supply of sterile water through a plastic tube that extends from the cartridge, as shown in FIG. 1A, and is connected to the RF generator. The windings of the vapor coil can be constructed from metal tubing, for example 18 gauge regular wall (RW) 304 stainless steel tubing, or 18 gauge thin wall (TW) plug drawn Inconel 625 tubing. The individual coil windings can be in physical contact and may be soldered or welded together to insure good electrical contact, although RF currents can pass through a sufficiently thin oxide layer separating windings.

Water in the vapor coil 120 is converted to steam by Ohmic heat produced by electrical current flowing around the circumference of the vapor coil. These currents are induced by RF current flowing in the concentric RF coil located in the delivery device handle. The alternating magnetic field produced by the currents in the RF coil may be strengthened by making the vapor coil from a magnetically permeable material. Since magnetic permeability of 300 series stainless steels is altered by cold working, it is difficult to obtain tubing lots having identical permeability. Because consistency in calorie output from device to device is very important, non-magnetic tubing is preferred in this application. Stainless steels like 304 may be annealed to eliminate magnetic properties, or a non-magnetic steel such as Inconel 625, MP35N, or Elgiloy may be chosen for the vapor coil. Inconel 625 is desirable because its electrical resistance is nearly independent of temperature over the range of temperatures (20° C.-350° C.) that may be experienced at the distal (steam) end of the vapor coil, enabling consistent vapor delivery from shot to shot and device to device.

One or more electrical leads may extend from the disposable cartridge along with the sterile water line. The wires can be plugged into the RF generator and may supply signals from/to an EPROM within the cartridge to supply cartridge identification and usage data. Other wires in this cable may supply signals from thermocouples located on the vapor coil within the cartridge and/or other diagnostic data from the cartridge. In another embodiment, EPROM and thermocouple wires may comprise a small cable that extends from the disposable cartridge and plugs into the non-disposable handle, and therethrough to the main delivery device handle cable. Alternatively, data may be inductively coupled from the cartridge without the need for physical leads, as disclosed below.

Figure 3:
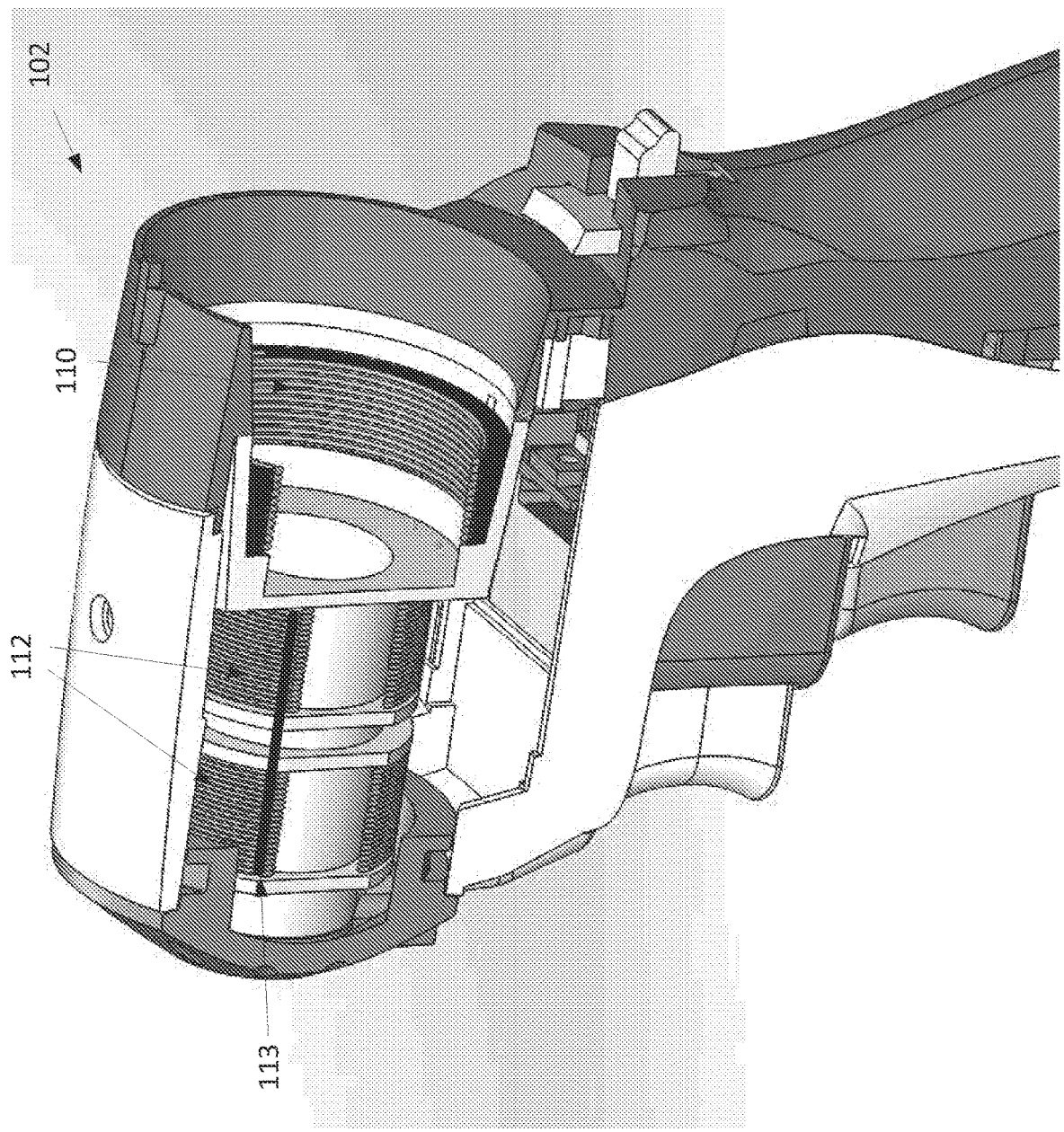
FIG. 3 shows a reusable handle of the vapor delivery device.
Figure 5:
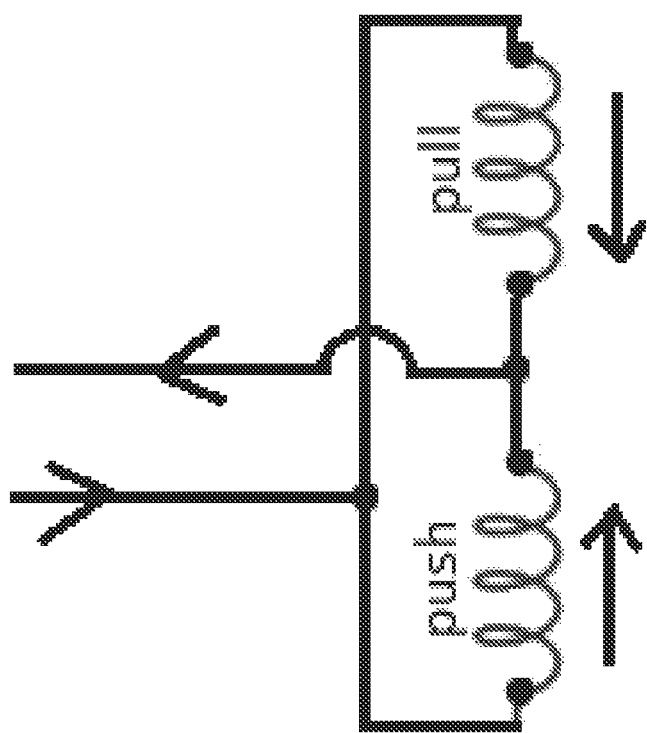
FIG. 5 shows the direction of current passed through push and pull coils of a magnetic actuator of the vapor delivery device.

The reusable handle portion 102 of the delivery device is shown in more detail in FIG. 3. The solenoid coils are configured in a push/pull configuration relative to the needle driver magnet shown in FIG. 2B. In the fully retracted needle position, a proximal end of the needle driver magnet is aligned with the proximal/push solenoid coil 112. In the fully extended needle position, a distal end of the needle driver magnet is aligned with the distal/pull solenoid coil 112. Current can be passed in opposite directions in the push and pull coils as shown in FIG. 5. The push coil sets up a magnetic field that repels the opposite polarity needle driver magnet out of the coil. Because of the repulsion, the magnet is not in stable equilibrium along the push coil axis, and is prone to lateral movements that could increase contact between the needle driver magnet and its surroundings, and increase frictional resistance to axial advancement. The pull coil creates a magnetic field that attracts the needle driver magnet into the pull coil. The pull coil attracts the needle driver magnet to the axis of the coil, and thereby removes the instability of the push coil. The combination of push and pull coils approximately doubles the force exerted by a single coil. The push/pull pair of coils also makes the retract force identical to the advance force simply by reversing the direction of current to the coil pair, as seen in FIG. 5.

FIG. 3 shows a potential location of the linear magnet position sensor 113 adjacent the solenoid coils. The linear magnet position sensor is configured to detect the magnetic field created by the needle driver magnet. A smaller magnetic field is created by the solenoid coils. The fields created by the two solenoid coils cancel each other on average and on the center plane between the coils. The linear magnet position sensor voltage output is a linear function of the position of the magnet (and the needle attached to the magnet). A onetime calibration can be performed to convert the sensor voltage to magnet position, relative to its most proximal position.

The RF coil 110 shown in FIG. 3 is designed to lie as close as possible to the vapor coil (vapor coil 120 of FIG. 2B) when the disposable cartridge is inserted into the handle portion 102, thereby providing the maximum induction of current in the vapor coil. The relationship between the RF coil and vapor coil in an assembled device is illustrated in FIG. 10. In one embodiment, the vapor coil comprises six turns of #18 TW Inconel 625 tubing, and the RF coil comprises 11 turns of #22 copper Litz wire comprised of individual strands of #44 copper magnet wire. These dimensions are chosen to optimize the electromagnetic coupling between the RF and vapor coils at an operating frequency in the range of 425 kHz to 475 kHz. The electrical insulation on the RF coil Litz wire can be 0.002" thick extruded PFA having a temperature rating of approximately 250° C.

Figure 4:
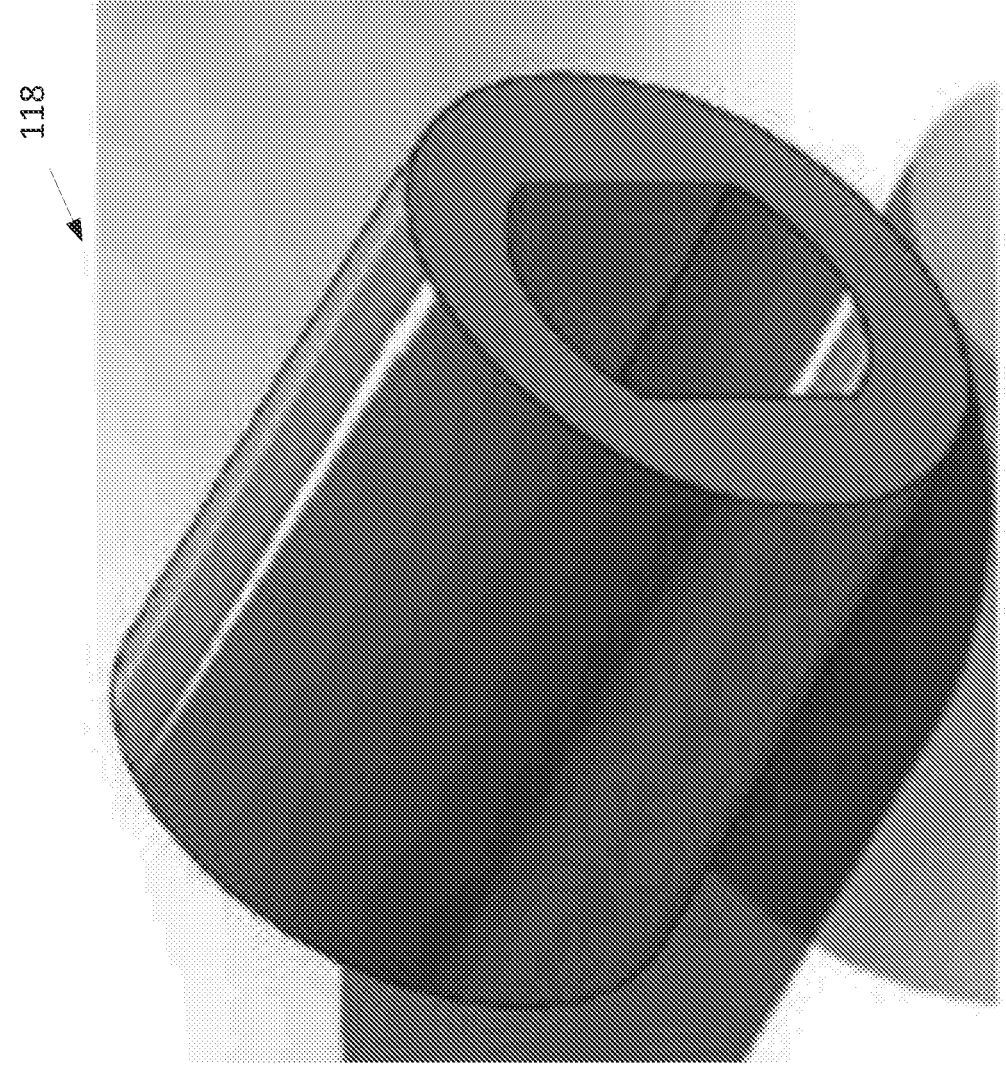
FIG. 4 shows a magnet of the vapor delivery device.

In one specific embodiment, shown in FIG. 4, the needle driver magnet 118 is made from grade N52 Neodymium-Iron-Boron, and has outer diameter dimensions of 15 mm and a length of 18 mm. The inside cut out is shaped to fit onto a needle attachment fixture. The residual induction of this specific oriented magnet material can be Br≈1.5 Tesla.

Other features of the reusable delivery device handle include a locking latch that prevents lateral movement of the cartridge within the handle, and detents that define every 30 degrees of rotation of the cartridge within the handle.

Increased Needle Length and Pulse Delivery

Figure 6A:
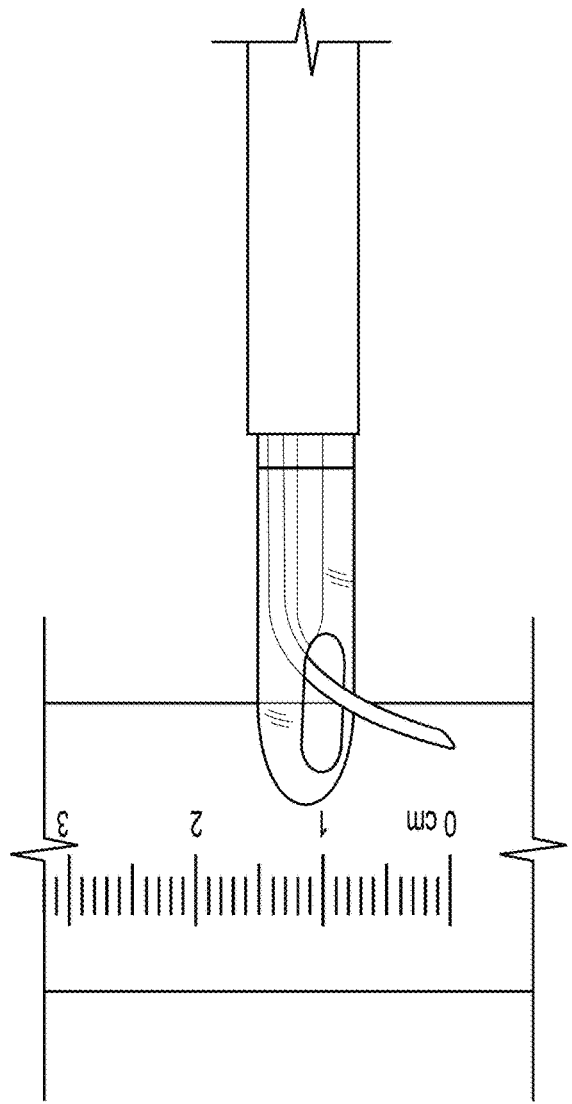
FIGS. 6A-6B show vapor needle deployment lengths moving from a BHP device to a cancer device.
Figure 6B:
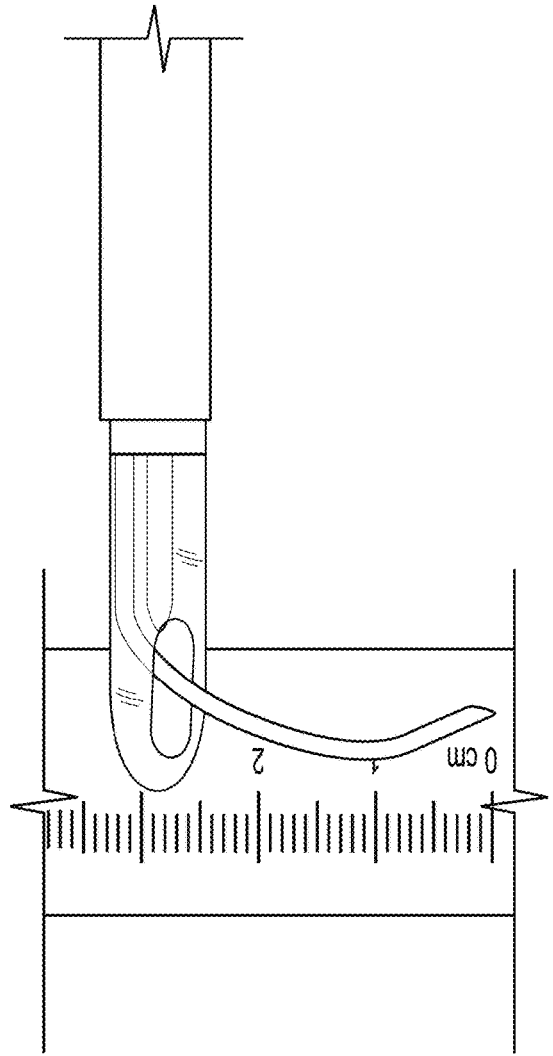

Since vapor for cancer therapy needs to reach peripheral lobes of the prostate from within the urethra, the vapor needle must extend further from the vapor delivery needle than for BPH procedures. The position of the vapor needle following deployment through the urethral wall, and the position when the needle is fully extended is shown in FIGS. 6A-6B.

The increase from ~12 mm travel of the BPH vapor delivery needle (FIG. 6A) to ~24 mm for the cancer vapor delivery needle is accomplished by increasing needle length, and increasing the gap width between the two coils of the solenoid, as shown in FIG. 7. For example, the solenoid coils of a BPH device can each comprise 408 turns of #30 magnet wire resulting in a needle travel of ~12 mm, and the solenoid coils in the cancer device can each comprise 605 turns of #28 magnet wire resulting in a needle travel of ~24 mm. In some embodiments, the needle cannot extend beyond 24 mm to avoid puncturing through the capsule of the prostate. However, the force required to overcome friction and deploy the needle with enough force to puncture the urethral wall cannot be achieved with the #30 gauge coils of the BPH system. In one embodiment, the force is increased by winding the bobbins with more turns of a lower gauge wire. The resistance remains the same for the cancer and BPH coils, and is chosen to optimize the current delivered from the generator 24 volt power supply.

Figure 8:
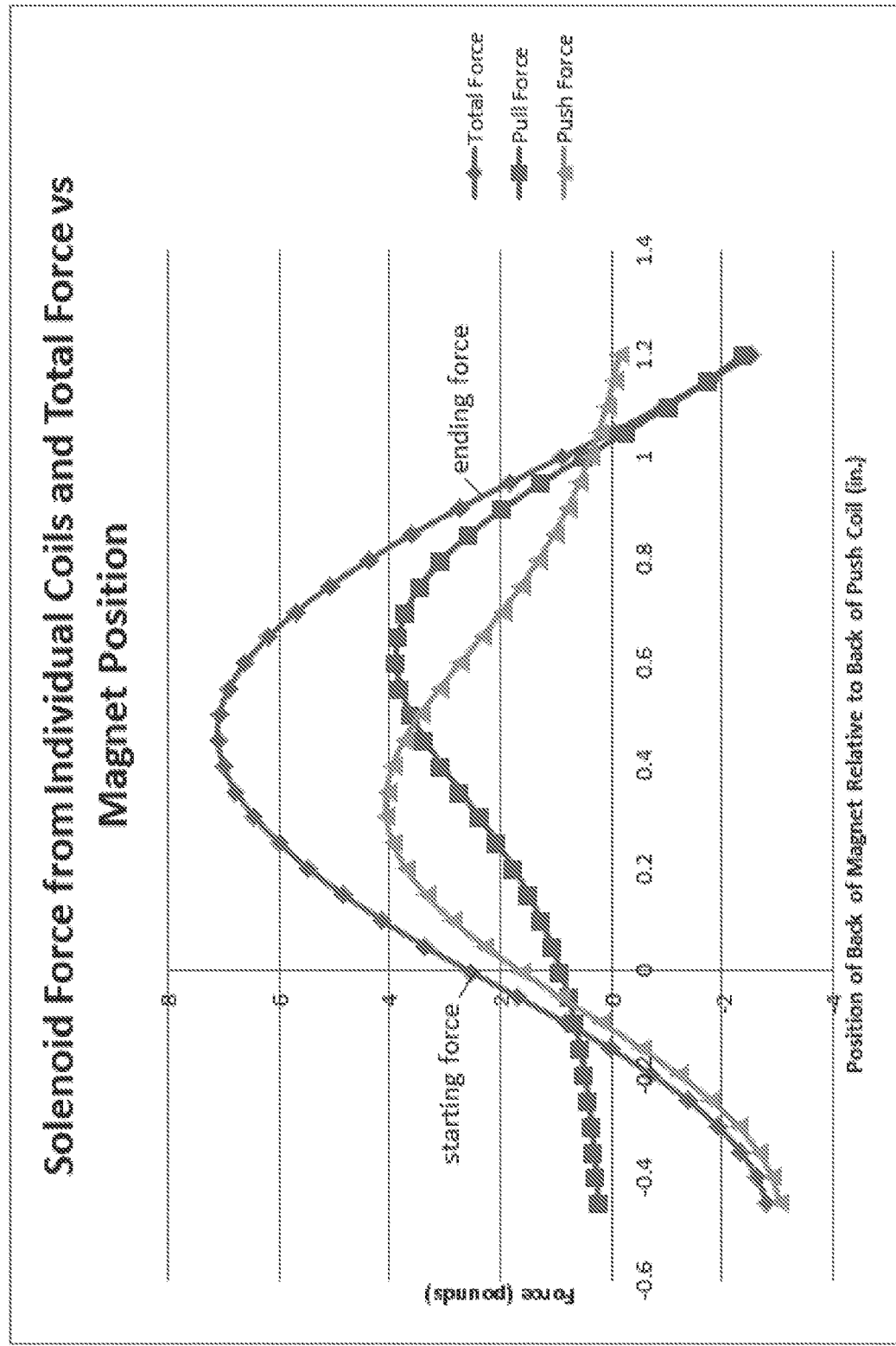
FIG. 8 shows resulting force versus magnet position.

Since the diameter of #28 gauge wire is slightly larger than the diameter of #30 wire, placing more turns of #28 wire requires increasing the outside diameter of the bobbin and reducing the bobbin inside wall thickness. The resulting calculated force versus magnet position is shown in FIG. 8, showing that the initial force for deploy and retract exceeds two pounds, enough to overcome friction. The peak force is 7.1 pounds, which is more than the peak BPH needle force. More force is achieved by using a power supply that can deliver more current, and optimizing the solenoid coil wire gauge for increased force. The power delivered to the solenoid (voltage times current) may be in the range of 100 Watts to 250 Watts, and the current is ON for a time ranging from 10 msec to 250 msec, and preferably in the range of 50 msec to 150 msec.

In one embodiment, separate disposable cartridge portions can be provided for BPH and prostate cancer vapor delivery procedures, using the same reusable handle portion. The respective disposable cartridge portions can include varying vapor delivery needle lengths depending on the procedure. In an alternative embodiment, the distance between the solenoid coils in FIG. 7 may be adjustable by the operator to select needle delivery lengths appropriate for both BPH and cancer procedures, while using the same disposable cartridge portion.

As described above, the vapor delivery device can be inserted transurethrally into the patient to gain access to the prostate. The vapor delivery needle can be deployed across the wall of the urethra, and advanced to a most distal location within the prostate, guided by a real time ultrasound image of the vapor delivery needle in the prostate. Vapor therapy may be delivered during advancement or during subsequent needle retraction. The user would prefer to advance the vapor delivery needle in small incremental steps, rather than very rapid deployment over a large distance as happens in the initial deployment. To achieve this goal, pulses of current can be delivered to the solenoid coils from the RF generator in response to the user depressing a trigger on the handle portion of the device. A magnetic position sensor can be used to measure the movement of the magnet and the vapor delivery needle, and to control the size of the incremental steps. In a preferred embodiment, each pulse of current deploys the needle by one mm, and the rate that pulses are delivered when the trigger is depressed is between one and five pulses per second. Both of these parameters can be user-adjustable.

As seen in FIGS. 6A-6B, the tip of the vapor delivery needle can be blunted, which may be achieved by needle design or by removal of material on the sharp tip. The needle can be designed to be sharp enough, and the force is large enough to penetrate the wall of the urethra during initial deployment, but dull enough so that the pulsed needle advance steps cannot force the needle through the prostate capsule. Impingement of the needle tip on the prostate capsule may be observed by the user as "tenting" on the ultrasound image. A second indication can be provided by the needle position sensor if it records an abnormally small needle advance after a pulse is applied. The system can lock out further advance steps and/or provide the user with a warning message.

Figure 9:
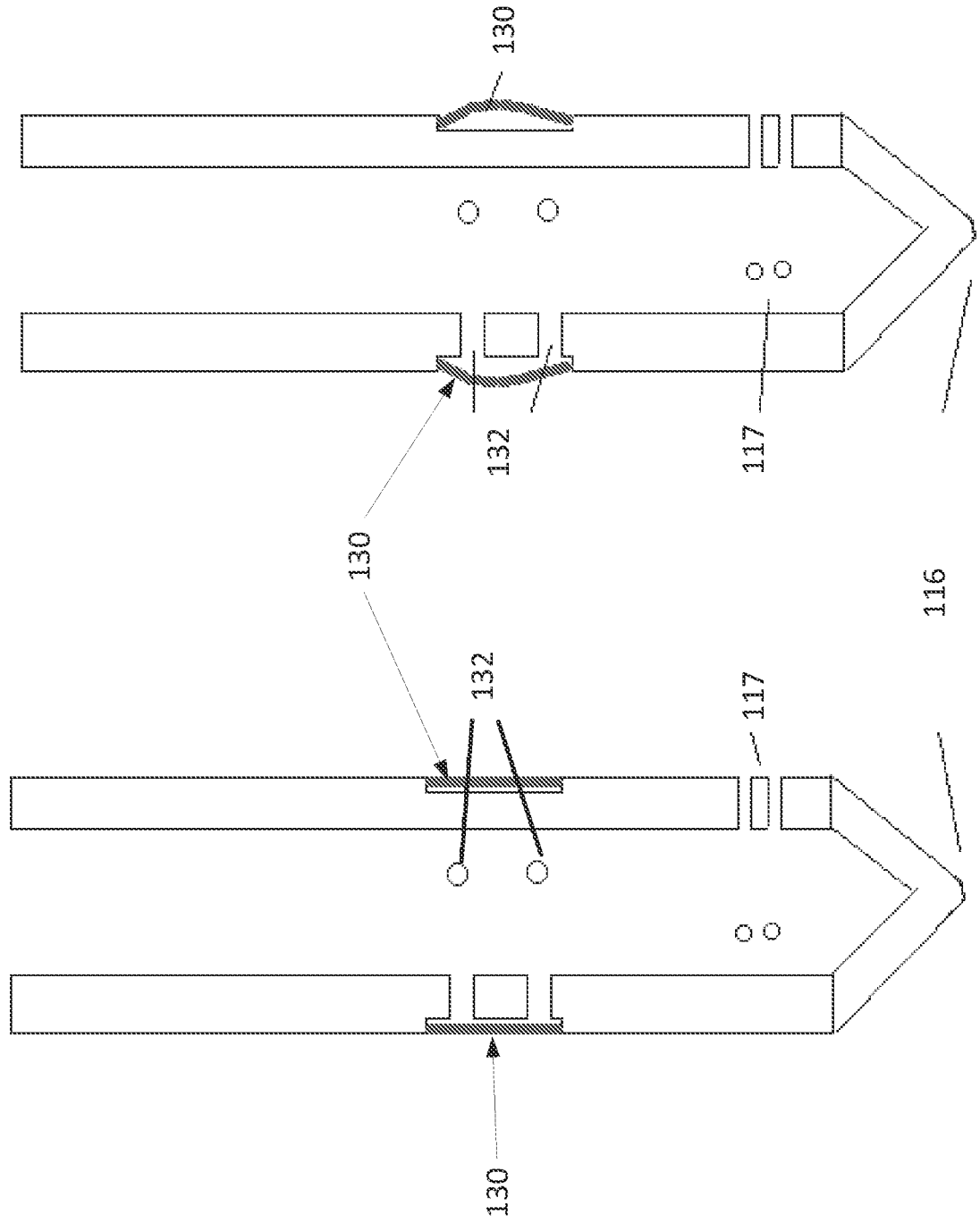
FIGS. 9A-9B show a technique for preventing vapor leakage.

In some procedures, it may be difficult to prevent vapor from leaking out of the needle puncture hole in the urethral wall. Movement of the delivery device and needle following puncture may enlarge the entry hole and facilitate vapor leakage. A technique for preventing vapor leakage is shown in FIGS. 9A-9B. In this embodiment, an expandable balloon material 130 is placed in an indent in the vapor delivery needle 116 at a distance of 4 to 24 mm proximal of the vapor delivery holes. During vapor delivery through vapor ports 117, the vapor can also enter the balloon 130 via holes 132 in the needle wall, and the balloon inflates to impinge upon tissue adjacent the needle and block vapor from leaking back out of the puncture site. The balloon material may be non-compliant and expand to a diameter set in production. Non-compliant balloon materials may be selected from PET (polyethylene terephthalate), nylon or other materials used for non-compliant medical balloons. The balloon material and thickness may be selected to provide thermal insulation between the vapor and surrounding tissue.

The number of vapor delivery holes and their diameter may be selected for a specific application. FIGS. 9A-9B show a needle having three rows of two vapor delivery holes. The shorter hole length provides more precise targeting of vapor delivery, which may be especially important when treating small peripheral zones or portions of zones that are narrow.

Improvements in Consistency of Therapy Delivery

The calorie output of the vapor delivery device of this invention is related to the power input of the RF generator during therapy delivery through an efficiency coefficient. Calorie output will be consistent from shot to shot if the power delivered is a constant, independent of changes in component values due to the thermal cycling of the device. Calorie output will be consistent from device to device if the input power is always the same for a given therapy, and if the efficiency coefficient is consistent from device to device. Device to device consistency is achieved through consistency of device manufacturing. In addition, consistency improves as the power coupling efficiency approaches 100%, provided that the input power is held constant. In other words, variations in device parameters have a diminishing effect on output as the percentage of the constant input power delivered to the output approaches 100%.

The RF coil 110 and vapor coil 120 of FIG. 10 have advantages for efficient and consistent therapy delivery. First, the relatively small number of turns on the vapor coil (6 turns shown in FIG. 10) means that excess heat generated at the distal end of the vapor coil may be conducted back through the thermally conductive metal of the six windings to pre-heat room temperature water entering the coil. It has been observed that the outlet temperature of the cancer vapor coil is lower than the outlet temperature of the BPH vapor coil for a given calorie output from the devices, presumably due to the thermal feedback. In addition, changes in the transformer coupling coefficient between the RF and vapor coils, that are caused by changes in the separation between the coils, are smaller for larger diameter coils.

Vapor Delivery System Sensors

The temperature of the vapor at the outlet of the vapor coil and the temperature of the vapor coil can be measured and monitored continuously by the system controller. Temperatures that fall outside set ranges can indicate damage to the vapor coil or inadequate delivery of vapor therapy, and can trigger automatic shut downs and guidance to the user on corrective actions. For example, an over temperature may indicate a kink or blockage in the water line tubing. An under temperature may indicate loss of RF power to the RF coil. The semi-disposable design of the described device lends itself to wireless sensors in which temperatures within the disposable cartridge are measured and communicated through wireless read out mechanisms in the delivery device handle. The wireless approach enables free rotation of the disposable within the handle, an important clinical feature that comes with no additional cost.

Figure 11:
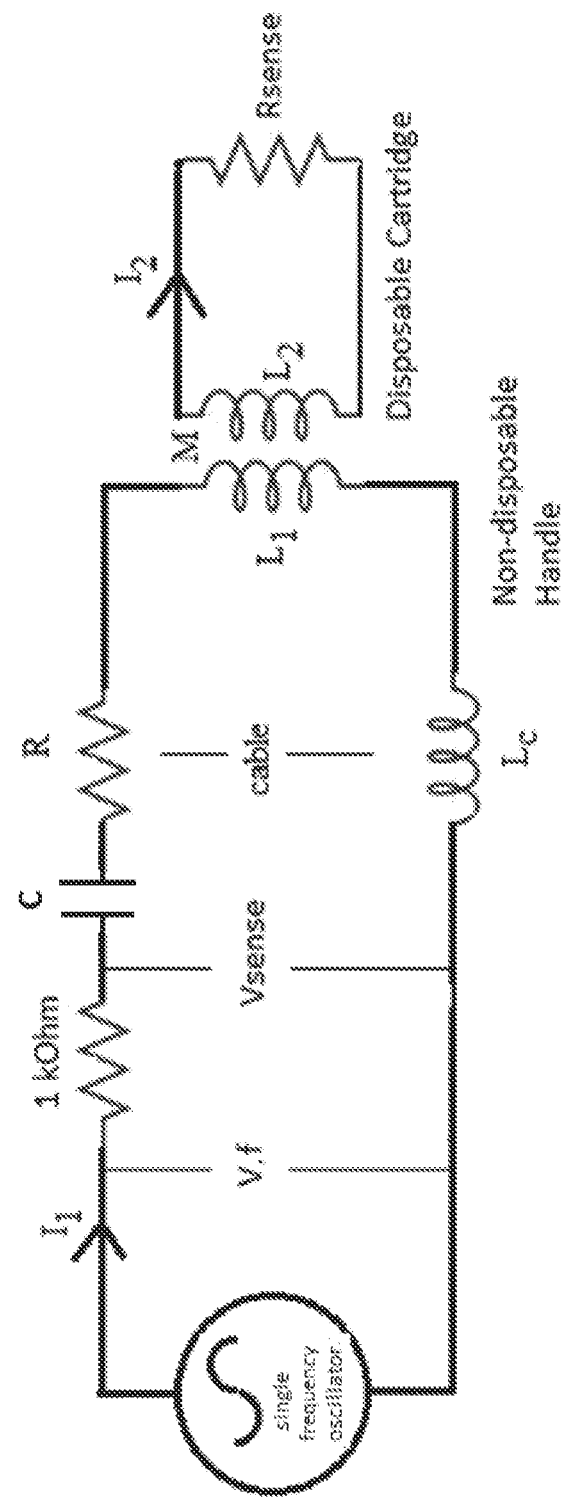
FIG. 11 shows an equivalent circuit for read out of the outlet tube RTD.

FIG. 11 shows the equivalent circuit for the temperature read out of the exiting vapor RTD. With the proper choice of circuit parameters it can be shown that the sensed voltage is a monatonic function of Rsense, the resistance of the copper wire RTD, which is a linear function of temperature through the temperature coefficient of copper wire. The expression for Vsense is inverted to give a formula for the temperature of the inner coil as a function of the sensed voltage Vsense. Typically, the single frequency of the oscillator is chosen to be distinct from any other frequencies that may be present in a procedure room, including the generator frequency. On the other hand, in one embodiment, the single frequency oscillator in FIG. 11A may be taken as a small fraction of the RF power supply voltage to reduce cost and minimize the number of components. In this case, care must be taken to manage any inductive pick-up from the RF coil during therapy.

The 1 kOhm resistor in FIG. 11 converts the single frequency oscillator voltage to a single frequency current source. The oscillator and 1 kOhm resistor may be replaced by a single frequency current source in FIG. 11. Single frequency current in the range of 10 mA to 100 mA will provide excellent signal to noise ratio in the Vsense measurement and the outlet temperature reading computed from Vsense. The temperature is an average over the 0.5" length of the sensor winding. This spatial average smooths fluctuations in temperature, which can occur in spots due to the erratic behavior of steam at the outlet.

Wireless read/write RFID tags are available commercially. Some of these are also capable of making temperature measurements. If added to the disposable cartridge, such devices must be economically priced. In another embodiment, an ID of the disposable cartridge is read by the RF generator but written to an e-cloud via an internet connection to the RF generator. All generators in service can connect to the cloud before each therapy procedure to retrieve usage information for the disposable device that has been inserted into the delivery device handle. At the conclusion of therapy, the number of therapy shots delivered by that device would be relayed to and stored in the cloud.

Methods of Using the Transurethral System

Figure 12:
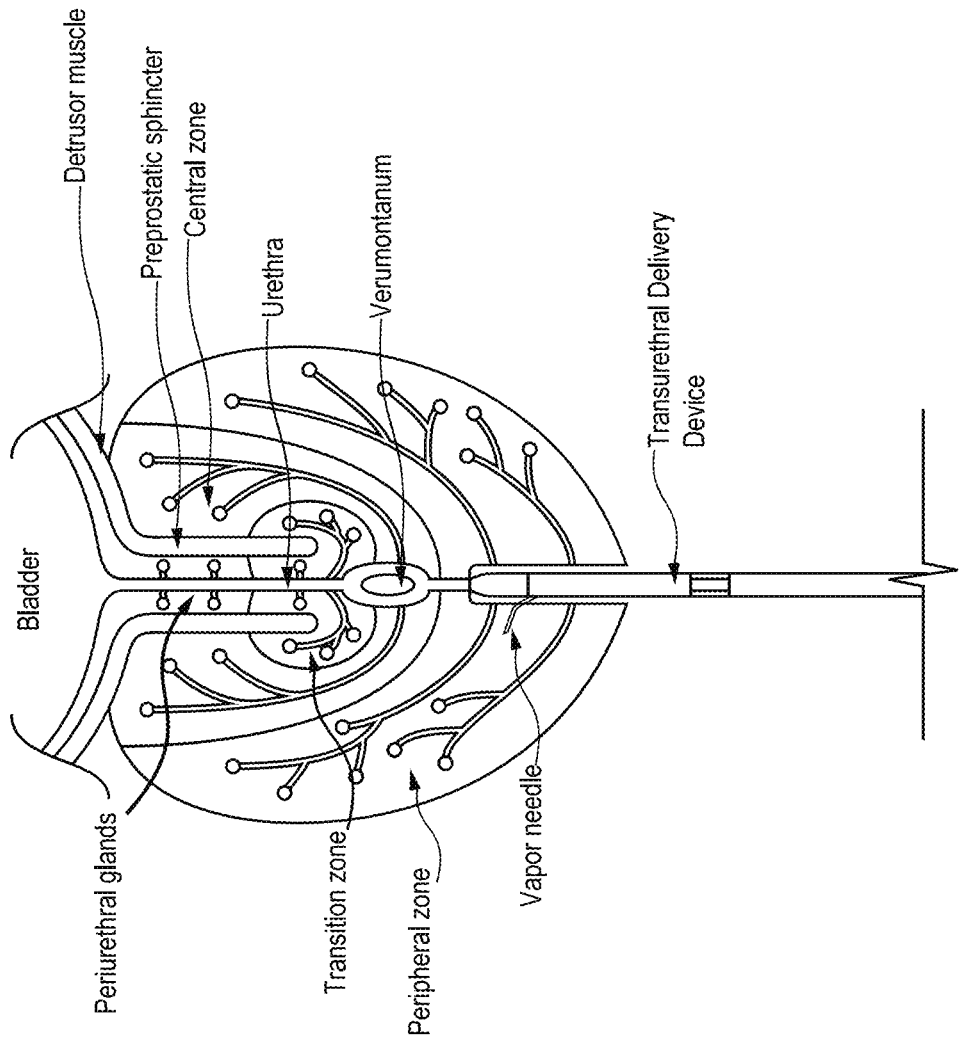
FIG. 12 shows a delivery device inserted into the prostatic urethra adjacent peripheral zone tissue.

FIG. 12 shows a delivery device inserted into the prostatic urethra adjacent peripheral zone tissue. Catheter placement may be guided by ultrasound images and the cystoscope camera, and further by the location of the access to the peripheral zone just behind the verumontanum, which is a visible landmark. The needle is first advanced through a travel distance of about 11 mm, as measured by the needle position sensor. The initial travel distance may be in the range of 6-12 mm, and must deploy the needle through the urethral lining into peripheral zone tissue.

Further depression of a deploy trigger switch causes the solenoid to activate current pulses at a rate that may be fixed or selected by the user, and may be in the range of one to five pulses per second. In one embodiment, the current pulses have the maximum amplitude that can be supplied by the system generator, and have an initial pulse width that may be fixed or user selected. In one embodiment the initial pulse width is T=1.5 msec. As the pulses are delivered to the solenoid, the needle position sensor measures the needle travel distance, increasing the width of the next pulse if the needle has traveled less than the target travel distance, e.g., 1 mm, and decreasing the width of the next pulse if the needle has traveled more than the target distance. On average, the needle moves the target distance with each pulse. The target distance may be fixed or user selected, and is 1 mm in a preferred embodiment. At any time the user may enable pulsed retract or full retraction. At any time, the user may release the trigger to halt the pulse advance/retract of the needle, for example to delivery vapor therapy. The output of the needle position sensor may be displayed so the user knows the distance along the needle between the needle tip and delivery device shaft.

A safety feature can be implemented that limits the pulse width, and therefore the force imparted to the needle, to a value that cannot penetrate a prostate capsule. If the needle has traveled less than the target distance of 1 mm for N pulses in a row, a needle blockage can be indicated and the user is alerted. Alternatively, the vapor delivery needle can be prevented from further advancing if the needle blockage is indicated. The blockage may be due to the needle impinging on the outer capsule of the prostate, and the value of N is chosen to limit the pulse width to a safe maximum value, determined in tissue studies, for which the needle cannot penetrate healthy or cancerous capsules. N may be in the range of 4 to 10 pulses, and the corresponding maximum pulse width may be in the range of 2 to 5 msec. Users may verify that the needle has impinged upon a capsule by observing tissue tenting on an ultrasound image.

In alternative embodiments, the user may have direct control of the pulse width and the number of pulses per second. This manual needle movement mode may preserve the safety features of the automated mode described above.

Transurethral vapor therapy may be used in conjunction with thermocouples inserted through the perineum to the outside of the prostate capsule to warn of temperatures high enough to damage the nerves on the capsule outside surface. Saline may be delivered to the outside of the prostate capsule to cool and protect the nerves. On the other hand, transurethral prostate ablation therapy may be delivered in multiple shots, each short enough with enough time between shots to prevent significant thermal conduction through the capsule to the nerves. For example, individual therapy shots lasting ten seconds or less, with at least 30 seconds between shots, may result in thorough ablation of the prostate tissue without the need for thermocouple or saline injection needles on the outside of the capsule.

In some embodiments, the peripheral and transition zones may be treated separately. In other embodiments, the vapor delivery needle is long enough to reach cancerous peripheral zone tissues after penetrating through the transition zone. Therapy may be delivered during pulse deployment or pulse retraction to both the peripheral and transition zone tissues. In other embodiments, central zone tissues that are impinging upon the urethra may be ablated during a cancer therapy treatment. The central zone may be treated individually, or in some cases after penetration through the transition zone. Central zone and transition zone tissues may both be treated during one needle deployment or retraction.

In some embodiments, ultrasound imaging is employed to guide the delivery of vapor to prostate tissues. In addition, the measurement of needle position by the needle position sensor has sub-mm accuracy, and may be used to gauge the distance between therapy shots. It is important to space the delivery of vapor by distances that will provide overlapping lesions, but with enough separation between shots to prevent the excessive heating and potential conduction across the prostate capsule. In some embodiments therapy shots are delivered with a separation between shots of 1 cm.

Therapy methods and means disclosed in provisional patent application 720 may be employed in the transurethral procedures. For example, adding a sensor at the needle tip that senses tissue capacitance can discriminate between prostate and non-prostate tissue, and prevent vapor delivery to non-prostate tissue and prevent accidental penetration of the prostate capsule. Tissue type sensing may be used in conjunction with a needle/magnet position sensor to verify that the magnet is within prostate tissue, and in particular, to determine when the needle is adjacent the prostate capsule. Pre-operative images may be used to determine optimal puncture sites along the urethra, and the number of vapor therapy shots that should be delivered within each puncture site. A prescribed distance between therapy shots then allows transurethral prostate ablation procedures to be performed without external image guidance. The delivery device probe is advanced to prescribed locations in the urethra by identifying anatomical landmarks in the cystoscope image, as in a BPH procedure. The needle is advanced through the urethra wall to a prescribed distance, guided by the magnet/needle position sensor output and/or by markings on the needle that are visible through the cystoscope. Therapy may be delivered during needle advancement, or the needle may be advanced to the prostate capsule wall, as indicated by the sensors, and therapy delivered during retraction.

In another example, an electromagnetic sensor or transmitter placed at or near the needle tip can facilitate tracking the location of the tip relative to a pre-operative or real time image of the prostate. In the case of ultrasound a second sensor or transmitter may be placed adjacent the ultrasound transducer, so the location and orientation of the needle tip is known relative to the transducer, facilitating autofocus and image enhancements. Tracking of the needle tip can enable robotic steering or navigation of the needle. Advanced vapor therapy delivery systems can robotically advance the needle to a point on an image selected by the operator and deliver a prescribed vapor dose at that site. The tip of the delivery device needle may be steerable using pull wires, as used in other catheter systems. Image guidance with steering enables therapy to be delivered at locations that are optimally separated in a three-dimensional pattern. More exotic steering means may be employed, for example by attaching a magnet to the needle tip, and steering the tip using large, external magnets.

Although particular embodiments of the present invention have been described above in detail, it will be understood that this description is merely for purposes of illustration and the above description of the invention is not exhaustive. Specific features of the invention are shown in some drawings and not in others, and this is for convenience only and any feature may be combined with another in accordance with the invention. A number of variations and alternatives will be apparent to one having ordinary skills in the art. Such alternatives and variations are intended to be included within the scope of the claims. Particular features that are presented in dependent claims can be combined and fall within the scope of the invention. The invention also encompasses embodiments as if dependent claims were alternatively written in a multiple dependent claim format with reference to other independent claims.

What is claimed is:

1. A vapor delivery device, comprising: a handle portion having a lumen and an energy coil disposed in the lumen, wherein the energy coil is connectable to a source of energy, and wherein windings of the energy coil surround and define a longitudinally extending lumen; and a cartridge portion configured to be inserted into the lumen of the handle portion, wherein the cartridge portion comprises: a shaft configured to be inserted into a urethra; a vapor delivery needle disposed in the shaft; and a vapor coil in fluid connection with (a) the vapor delivery needle and (b) a fluid source; wherein, in an assembled configuration in which the cartridge portion has been inserted into the lumen of the handle portion, the vapor coil is within the lumen of the energy coil; wherein, in the assembled configuration, an entirety of the cartridge portion is rotatable, relative to the handle portion, from a first position to a second position, by a rotational connection between the cartridge portion and the handle portion; wherein, in each of the first position of the cartridge portion and the second position of the cartridge portion, upon delivery of a fluid from the fluid source to the vapor coil, a flow of energy from the source of energy through the energy coil inductively generates vapor in the vapor coil; and wherein the lumen of the handle portion includes a proximal opening and a distal opening, and wherein a distal end of the shaft of the cartridge portion is configured to be inserted into the proximal opening in order to align and position the vapor coil within the energy coil.

2. The vapor delivery device of claim 1, wherein the cartridge portion further includes a thermometer, and wherein the thermometer is in electrical contact with the handle portion in both the first position and the second position.

3. The vapor delivery device of claim 2, wherein the cartridge portion includes at least one conductive ring extending around an external surface of the cartridge portion, wherein the at least one conductive ring is electrically connected to the thermometer.

4. The vapor delivery device of claim 3, wherein the handle portion includes at least one canted coil, and wherein the thermometer is in electrical contact with the handle portion via a contact between the at least one conductive ring of the cartridge portion and the at least one canted coil.

5. The vapor delivery device of claim 3, wherein the at least one conductive ring is proximal of the vapor coil.

6. The vapor delivery device of claim 1, wherein, in the assembled configuration, a longitudinal axis of the cartridge portion extends through a central opening of the vapor coil.

7. The vapor delivery device of claim 1, wherein the vapor coil is wrapped around an outer surface of a body of the cartridge portion.

8. The vapor delivery device of claim 1, wherein, in the assembled configuration, the handle portion completely radially surrounds at least a portion of the cartridge portion.

9. The vapor delivery device of claim 1, wherein the first position is offset from the second position by at least 30 degrees.

10. A vapor delivery device, comprising: a handle portion having a lumen and an energy coil disposed in the lumen, wherein the energy coil is connectable to a source of energy, and wherein windings of the energy coil surround and define a longitudinally extending lumen; and a cartridge portion configured to be inserted into the lumen of the handle portion, wherein the cartridge portion comprises: a shaft configured to be inserted into a urethra; a vapor delivery needle disposed in the shaft; a vapor coil in fluid connection with (a) the vapor delivery needle and (b) a fluid source; a thermometer; and a conductive ring extending around an outer surface of the cartridge portion, wherein the conductive ring is electrically connected to the thermometer; wherein, in an assembled configuration in which the cartridge portion has been inserted into the lumen of the handle portion, the vapor coil is within the lumen of the energy coil; wherein, in the assembled configuration, an entirety of the cartridge portion is rotatable, relative to the handle portion, from a first position to a second position, by a rotational connection between the cartridge portion and the handle portion; wherein, in each of the first position of the cartridge portion and the second position of the cartridge portion, the conductive ring is in electrical contact with the handle portion; and wherein the lumen of the handle portion includes a proximal opening and a distal opening, and wherein a distal end of the shaft of the cartridge portion is configured to be inserted into the proximal opening in order to align and position the vapor coil within the energy coil.

11. The vapor delivery device of claim 10, wherein the handle portion includes at least one canted coil, and wherein the conductive ring is in electrical contact with the at least one canted coil in each of the first position and the second position.

12. The vapor delivery device of claim 10, wherein, in the assembled configuration, a longitudinal axis of the cartridge portion extends through a central opening of the vapor coil.

13. The vapor delivery device of claim 10, wherein the vapor coil is wrapped around an outer surface of a body of the cartridge portion.

14. The vapor delivery device of claim 10, wherein, in the assembled configuration, the handle portion completely radially surrounds at least a portion of the cartridge portion.

15. The vapor delivery device of claim 10, wherein the first position is offset from the second position by at least 30 degrees.

16. A vapor delivery device, comprising:
  a handle portion having a lumen and an energy coil disposed in the lumen, wherein the energy coil is connectable to a source of energy; and
  a cartridge portion configured to be inserted into the lumen of the handle portion, wherein the cartridge portion comprises:
    a shaft configured to be inserted into a urethra;
    a vapor delivery needle disposed in the shaft;
    a vapor coil in fluid connection with (a) the vapor delivery needle and (b) a fluid source; and
    a thermometer;
  wherein insertion of the cartridge portion into the handle portion aligns and positions the vapor coil into an alignment position within the energy coil, and places the handle portion and the cartridge portion into a fully assembled state;
  wherein, in the fully assembled state, the cartridge portion is rotatably coupled to the handle portion by a rotational connection such that the cartridge portion is rotatable relative to the handle portion while the vapor coil remains in the alignment position;
  wherein the rotational connection maintains an electrical contact between the handle portion and the thermometer of the cartridge portion, during rotation of the cartridge portion relative to the handle portion; and
  wherein the lumen of the handle portion includes a proximal opening and a distal opening, and wherein a distal end of the shaft of the cartridge portion is configured to be inserted into the proximal opening in order to align and position the vapor coil within the energy coil.

17. The vapor delivery device of claim 16, wherein the cartridge portion includes at least one conductive ring extending around an external surface of the cartridge portion, wherein the at least one conductive ring is electrically connected to the thermometer.

18. The vapor delivery device of claim 17, wherein the handle portion includes at least one canted coil, and wherein the electrical contact is between the at least one conductive ring of the cartridge portion and the at least one canted coil.

* * * * *